(12) United States Patent
Je et al.

(10) Patent No.: US 7,846,558 B2
(45) Date of Patent: Dec. 7, 2010

(54) BLUE LIGHT EMITTING COMPOUND AND ORGANIC ELECTROLUMINESCENT DEVICE USING THE SAME

(75) Inventors: Jong-Tae Je, Cheongju-si (KR); Sang-Hae Lee, Daejeon (KR); Sug-Kwang Hwang, Cheongwon-gun (KR); Seon-Keun Yoo, Jeungpyeong-gun (KR)

(73) Assignee: SFC Co., Ltd., Cheongwon-Kun, Chungbuk (KR)

( * ) Notice: Subject to any disclaimer, the term of this patent is extended or adjusted under 35 U.S.C. 154(b) by 797 days.

(21) Appl. No.: 11/820,876

(22) Filed: Jun. 21, 2007

(65) Prior Publication Data
US 2008/0203905 A1 Aug. 28, 2008

(30) Foreign Application Priority Data
Feb. 28, 2007 (KR) .................. 10-2007-0020637

(51) Int. Cl.
H01J 1/63 (2006.01)
C07C 211/50 (2006.01)
H01L 51/54 (2006.01)

(52) U.S. Cl. ............. 428/690; 428/917; 564/426; 313/504; 313/506

(58) Field of Classification Search ............... None
See application file for complete search history.

(56) References Cited

U.S. PATENT DOCUMENTS

| 2002/0121860 | A1* | 9/2002 | Seo et al. ............... 313/506 |
| 2003/0035978 | A1* | 2/2003 | Raychaudhuri et al. ...... 428/690 |
| 2004/0137270 | A1* | 7/2004 | Seo et al. ............... 428/690 |
| 2007/0114917 | A1* | 5/2007 | Funahashi et al. ........ 313/504 |
| 2007/0243411 | A1* | 10/2007 | Takashima et al. ........ 428/690 |
| 2007/0252511 | A1* | 11/2007 | Funahashi ............... 313/498 |
| 2009/0134781 | A1* | 5/2009 | Jang et al. ............. 313/504 |

FOREIGN PATENT DOCUMENTS

| KR | 10-2004-0057862 A | 7/2004 |
| WO | WO 2005/108348 A1 * | 11/2005 |
| WO | WO 2007/108666 A1 * | 9/2007 |

OTHER PUBLICATIONS

Thomas et al., Advanced Functional Materials, (2004), vol. 14, No. 4, pp. 387-392.*

* cited by examiner

*Primary Examiner*—Dawn Garrett
(74) *Attorney, Agent, or Firm*—Edwards Angell Palmer & Dodge LLP; Kongsik Kim

(57) ABSTRACT

A blue light emitting compound and an organic electroluminescent device using the compound are provided. The device exhibits improved color purity of blue emission and excellent life characteristics so as to be used to manufacture a full-color display.

9 Claims, 1 Drawing Sheet

BLUE LIGHT EMITTING COMPOUND AND ORGANIC ELECTROLUMINESCENT DEVICE USING THE SAME

CROSS-REFERENCE TO RELATED APPLICATION

The present application claims, under 35 U.S.C. §119, the benefit of Korean Patent Application No. 10-2007-0020637 filed Feb. 28, 2007, the entire contents of which are hereby incorporated by reference.

TECHNICAL BACKGROUND

1. Technical Field

The present invention relates to a blue light-emitting compound and an organic electroluminescent device comprising the compound. More specifically, the present invention relates to a blue light-emitting compound that can be used to fabricate an organic electroluminescent device with improved color purity of blue emission and excellent life characteristics, and an organic electroluminescent device fabricated using the blue light-emitting compound.

2. Background Art

As displays have become larger in size in recent years, there is an increasing demand for flat panel display devices that take up as little space as possible. Liquid crystal display devices as representative flat panel display devices can be reduced in weight when compared to the prior art cathode ray tubes (CRTs), but have several disadvantages in that the viewing angle is limited, the use of backlight is inevitably required, etc. Organic light-emitting diodes (OLEDs) as a novel type of flat panel display devices are self-emissive display devices. Organic light-emitting diodes have a broad viewing angle, and are advantageous in terms of light weight, small thickness, small size and rapid response time when compared to liquid crystal display devices.

A representative organic light-emitting diode was reported by Gurnee in 1969 (U.S. Pat. Nos. 3,172,862 and 3,173,050). However, this organic light-emitting diode suffers from limitations in its applications because of its limited performance. Since Eastman Kodak Co. reported multilayer organic light-emitting diodes in 1987 (C. W. Tang et al., Appl. Phys. Lett., 51, 913 (1987); and J. Applied Phys., 65, 3610 (1989)), remarkable progress has been made in the development of organic light-emitting diodes capable of overcoming the problems of the prior art devices.

Organic electroluminescent devices have superior characteristics, such as low driving voltage (e.g., 10V or less), broad viewing angle, rapid response time and high contrast, over plasma display panels (PDPs) and inorganic electroluminescent display devices. Based on these advantages, organic electroluminescent devices can be used as pixels of graphic displays, television image displays and surface light sources. In addition, organic electroluminescent devices can be fabricated on flexible transparent substrates, can be reduced in thickness and weight, and have good color representation. Therefore, organic electroluminescent devices are recognized as promising devices for use in next-generation flat panel displays (FPDs).

Such organic electroluminescent devices comprise a first electrode as a hole injection electrode (anode), a second electrode as an electron injection electrode (cathode), and an organic light-emitting layer disposed between the anode and the cathode wherein electrons injected from the cathode and holes injected from the anode combine with each other in the organic light-emitting layer to form electron-hole pairs (excitons), and then the excitons fall from the excited state to the ground state and decay to emit light. Organic electroluminescent devices have been applied to full-color displays. To obtain fill colors, it is necessary to arrange pixels, which emit light of three primary colors, i.e. green, red and blue colors, respectively, on a panel. Various methods have been suggested to arrange pixels on a panel. Examples of such methods include: (i) the arrangement of three types of organic electroluminescent devices emitting blue, green and red colors, respectively; (ii) the separation of light emitted from a white (a mixed color of red, green and blue (RGB) colors) light-emitting device into three primary colors through a color filter; and (iii) the use of light emitted from a blue organic light-emitting device as a source of fluorescence emission to convert the light to green and red light.

One important requirement is to provide a material capable of emitting blue light with high luminance, high efficiency and improved color purity. Hence, intensive researches have been made. For example, U.S. Pat. No. 6,455,720 describes a 2,2-(diaryl)vinylphosphine compound as a blue light-emitting material. Further, Korean Patent Laid-open Publication No. 10-2002-0070333 describes a blue light-emitting compound which has a diphenylanthracene structure in the center and an aryl-substituted specific structure at an end thereof, and an organic electroluminescent device using the blue light-emitting compound. However, the organic electroluminescent devices including the materials have insufficient luminescence efficiency and luminance.

Further, Korean Patent No. 525,408 discloses an organic electroluminescent device which uses a pyrene compound substituted with a diphenylamine derivative. This organic electroluminescent device, however, has poor color purity of blue emission (i.e., chromaticity coordinates of x=0.146 and y=0.205), which makes it difficult to achieve deep blue light emission and be applied for full-color displays producing natural colors.

Additionally, U.S. Pat. No. 5,153,073 discloses an organic electroluminescent device which uses a pyrene compound substituted with a diphenylamine derivative. However, this device substantially emits bluish green light due to its poor color purity of blue emission, and partially emits bluish light with low luminance.

Also, PCT Publication No. WO 2004/083162 A1 discloses an organic electroluminescent device which uses a pyrene compound substituted with a diphenylamine derivative. However, this device has poor color purity of blue emission and is not suitable for the manufacture of full-color displays producing natural colors.

Further, PCT Publication No. WO 2005/108348 A1 discloses an aromatic amine derivative having a structure in which a pyrene compound is directly substituted with a substituted or unsubstituted diphenylamine group. However, the aromatic amine derivative emits bluish green light due to the presence of an aryl or alkyl group directly bonded to the pyrene ring.

There is thus a need for a novel blue light-emitting compound and an organic electroluminescent device comprising the compound.

The information disclosed in this Background section is only for enhancement of understanding of the background of the invention and should not be taken as an acknowledgement

SUMMARY OF THE INVENTION

In one aspect, the present invention provides a blue light-emitting compound of Formula 1:

(1)

wherein $A_1$ to $A_4$ are each independently a $C_6$-$C_{20}$ aryl group which is unsubstituted or substituted with a group selected from the group consisting of $C_1$-$C_{10}$ alkyl, $C_1$-$C_{10}$ alkoxy, cyano, $C_1$-$C_{10}$ alkylamino, $C_1$-$C_{10}$ alkylsilyl, halogen, $C_6$-$C_{10}$ aryl, $C_6$-$C_{10}$ aryloxy, $C_6$-$C_{10}$ arylamino, $C_6$-$C_{10}$ arylsilyl and hydrogen, or a $C_4$-$C_{19}$ heteroaryl group containing at least one heteroatom selected from N, S and O atoms, with the proviso that the substituents of $A_1$ to $A_4$ include at least one cyano group and at least one alkylsilyl or arylsilyl group; and n is 0 or 1.

A preferred blue light-emitting compound may be selected from the group consisting of the following compounds:

-continued
BD 07
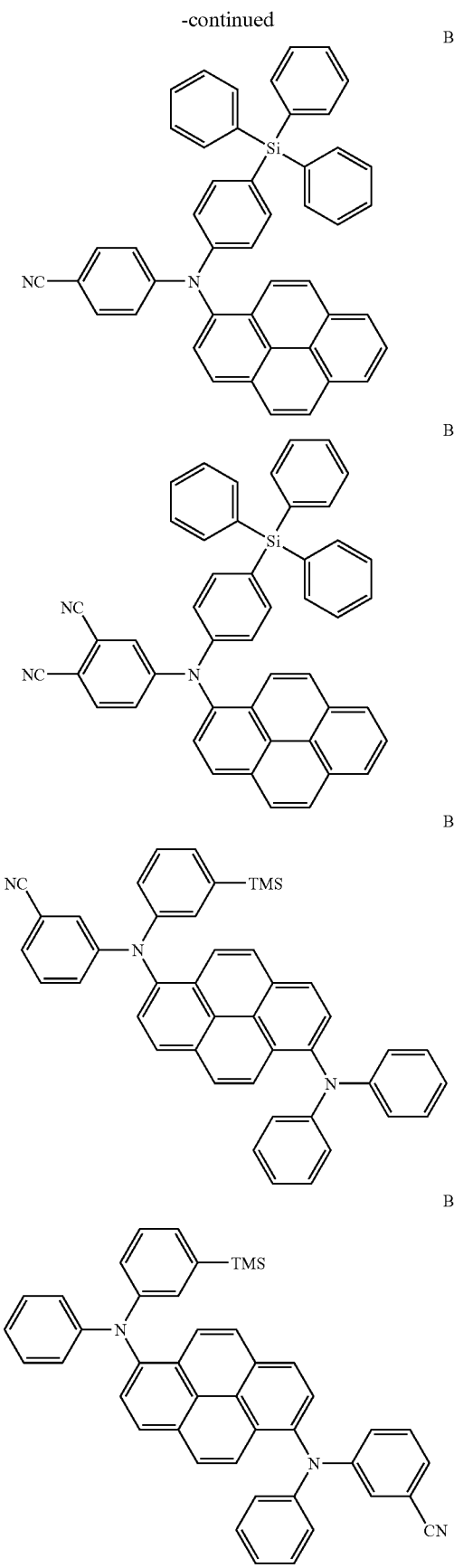
BD 08
BD 09
BD 10
-continued
BD 11
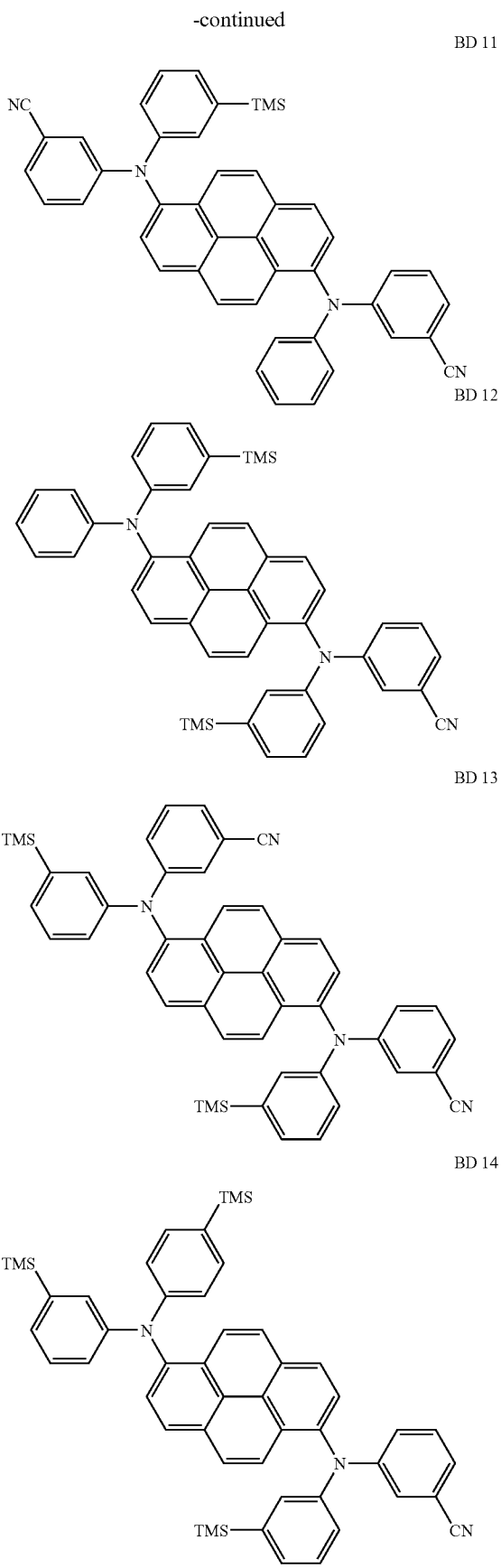
BD 12
BD 13
BD 14

-continued
BD 15
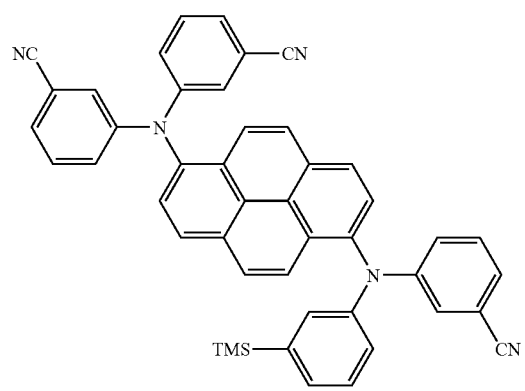
BD 16
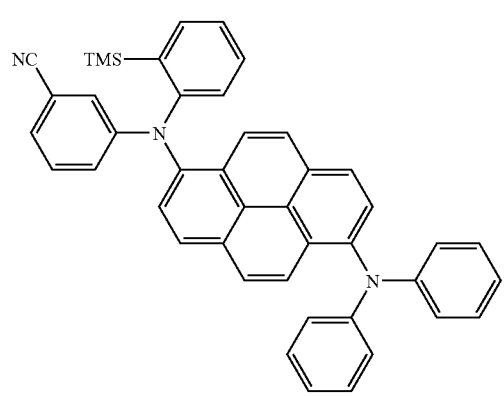
BD 17
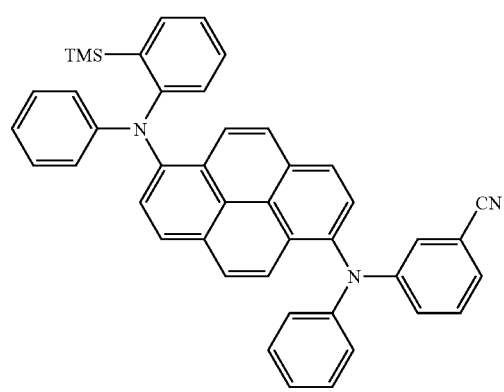
BD 18
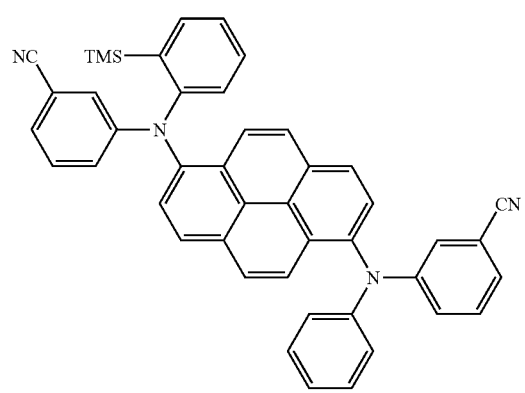
-continued
BD 19
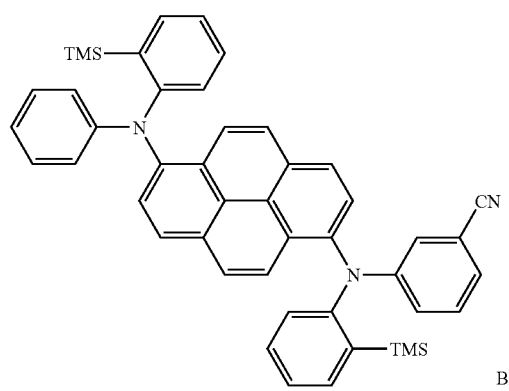
BD 20
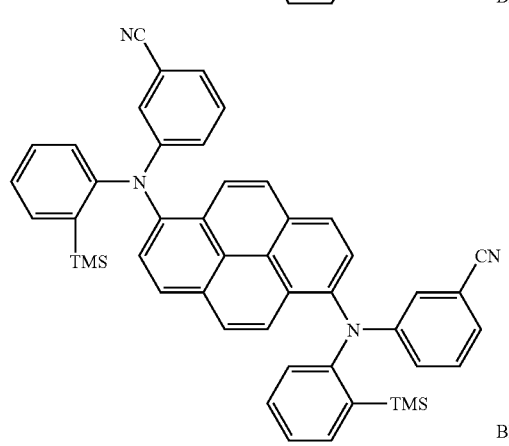
BD 21
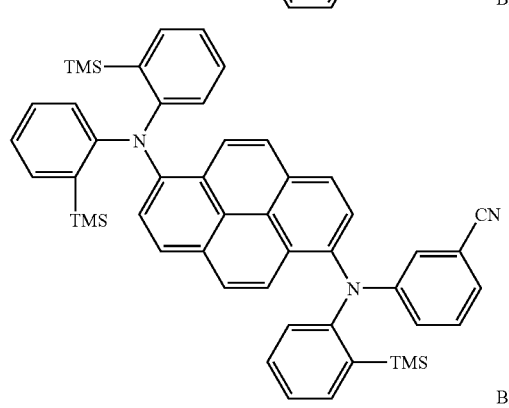
BD 22
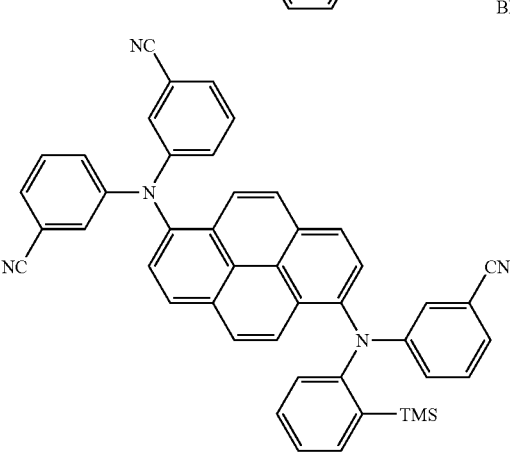

-continued
BD 23
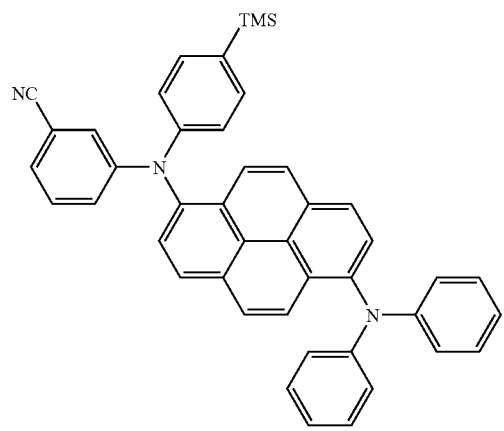
BD 24
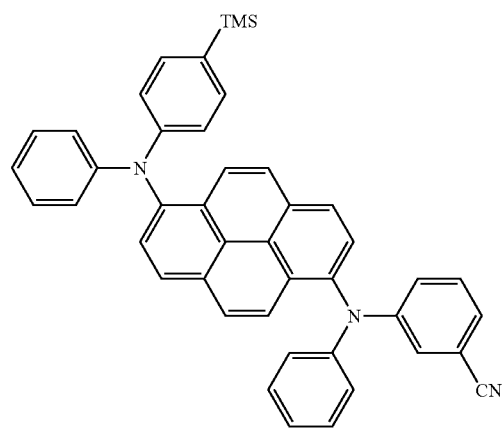
BD 25
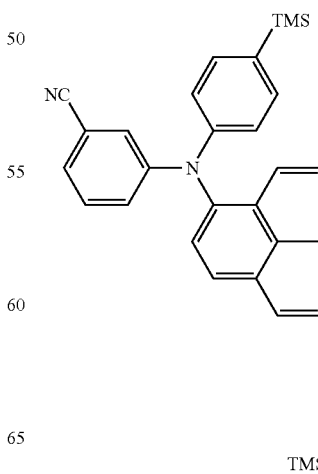
-continued
BD 26
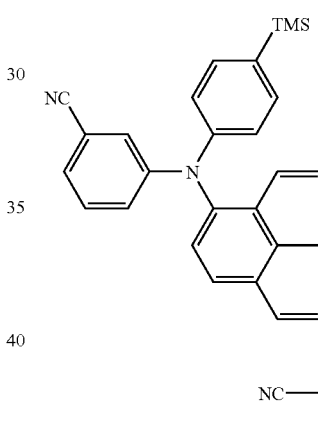
BD 27
BD 28

-continued
BD 29
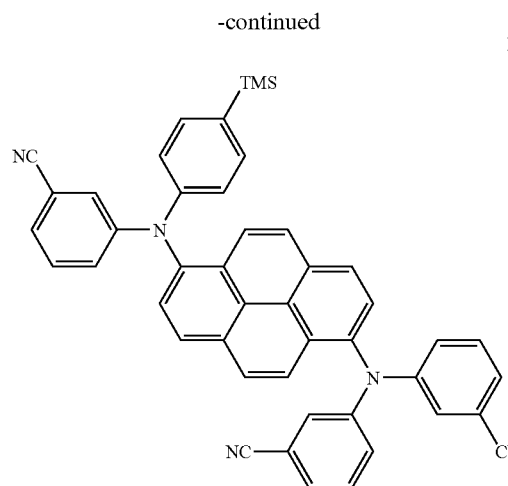
BD 30
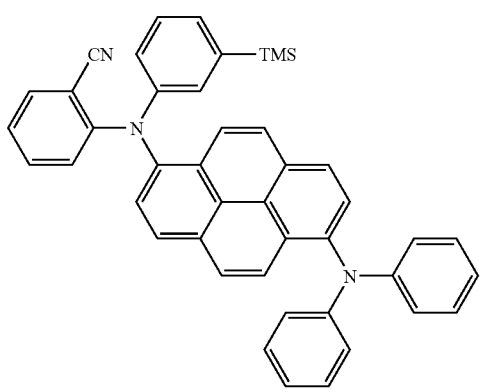
BD 31
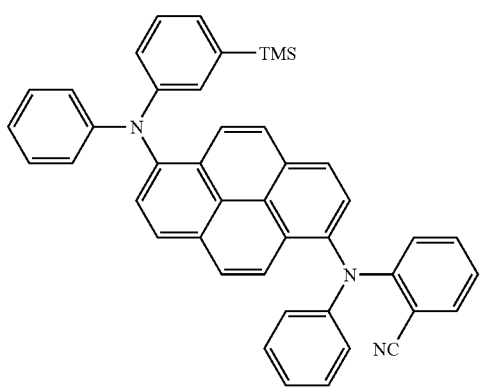
BD 32
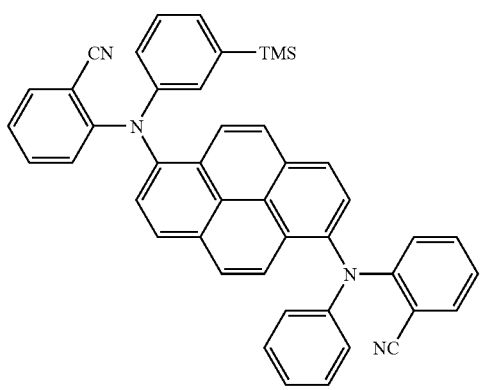
-continued
BD 33
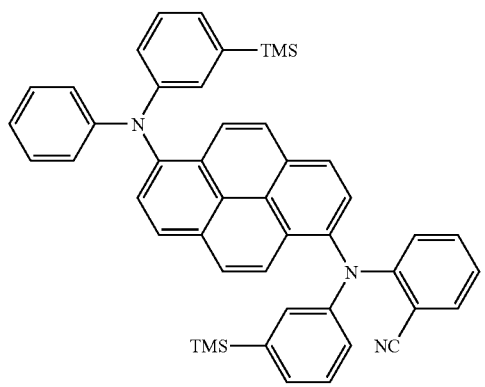
BD 34
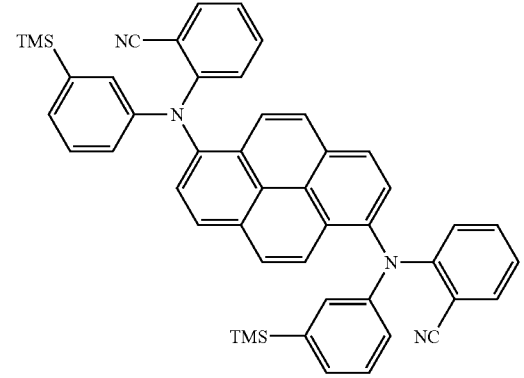
BD 35
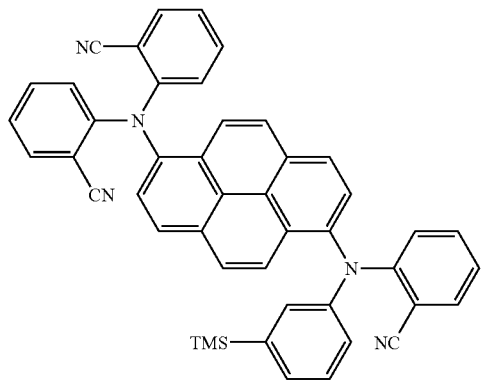
BD 36

-continued
BD 37
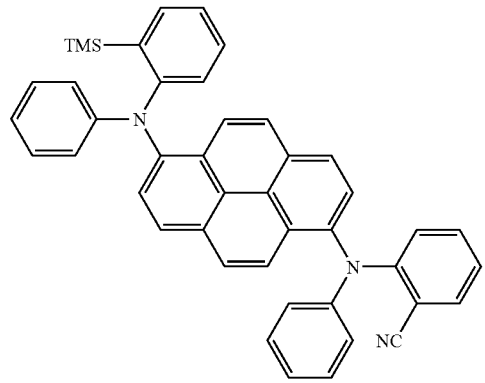
BD 38
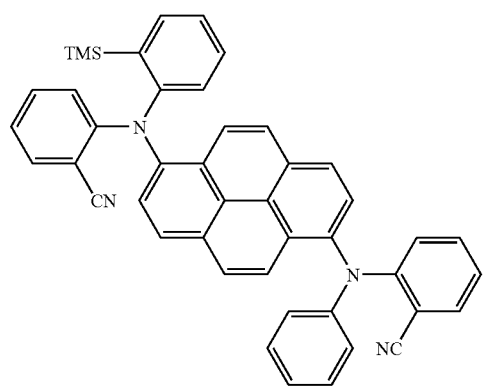
BD 39
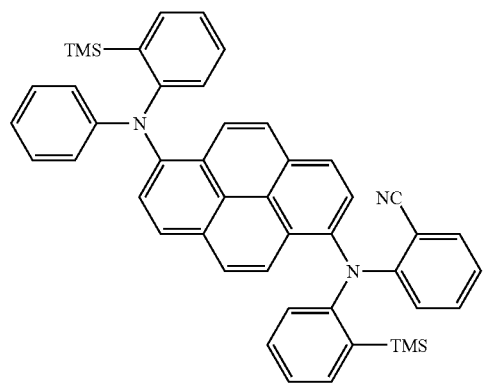
BD 40
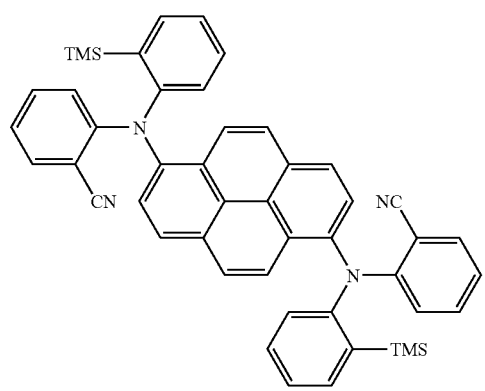
-continued
BD 41
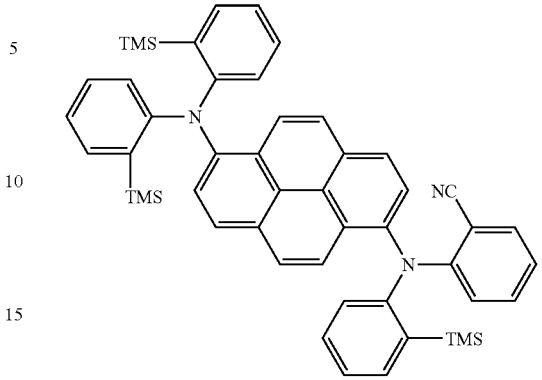
BD 42
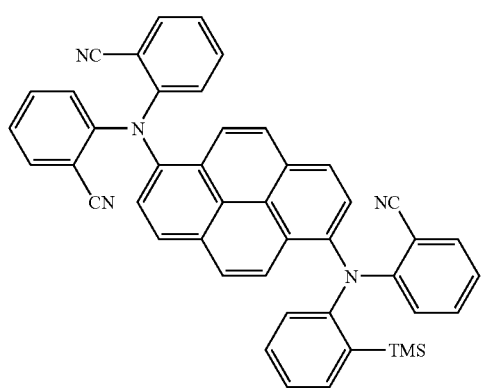
BD 43
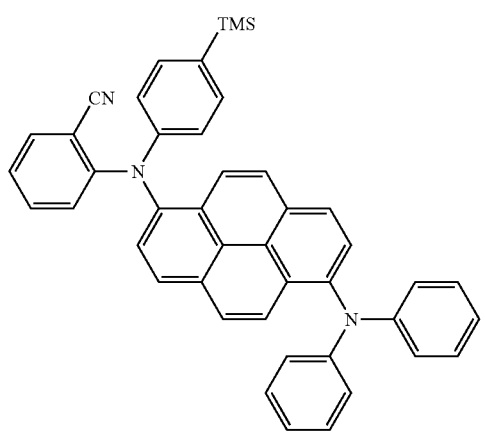
BD 44
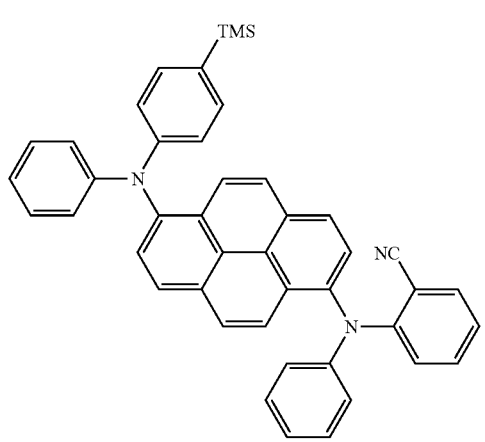

-continued
BD 45
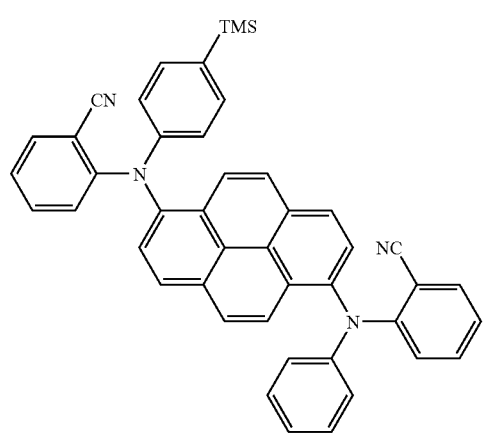
BD 46
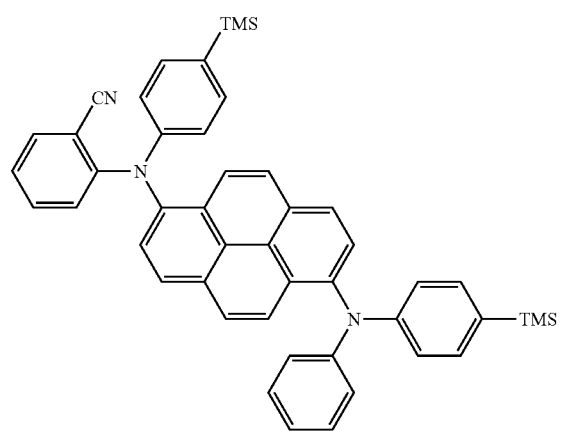
BD 47
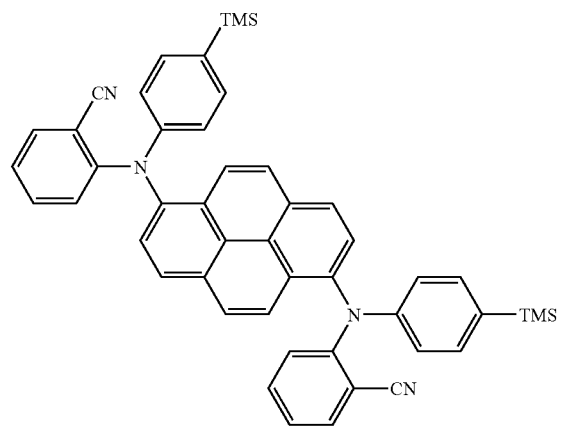
-continued
BD 48
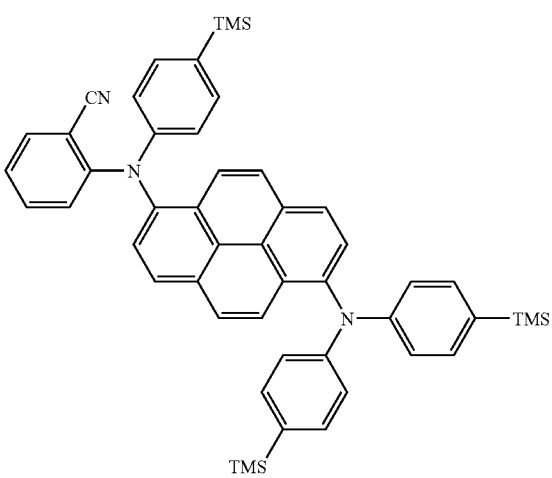
BD 49
BD 50
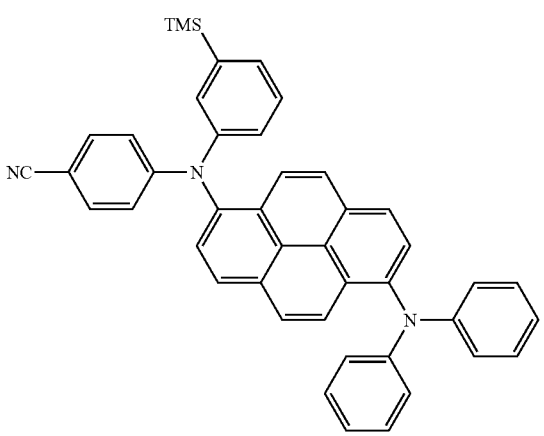

-continued
BD 51
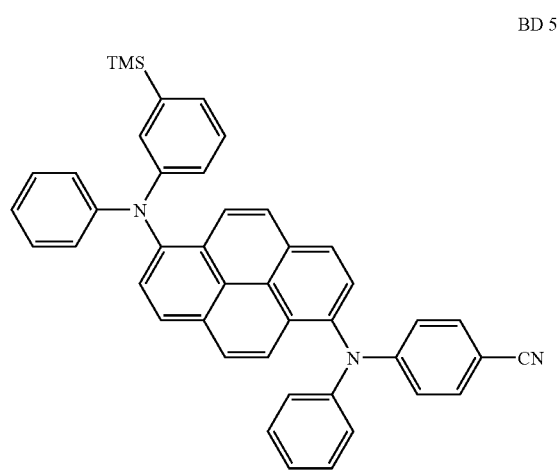
BD 52
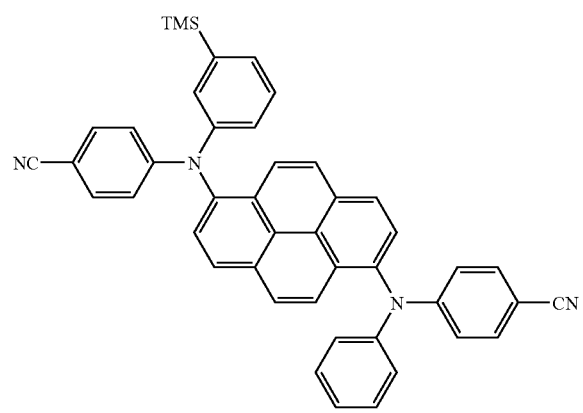
BD 53
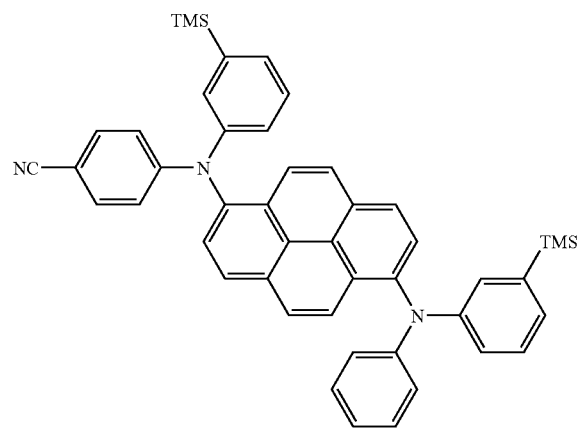
-continued
BD 54
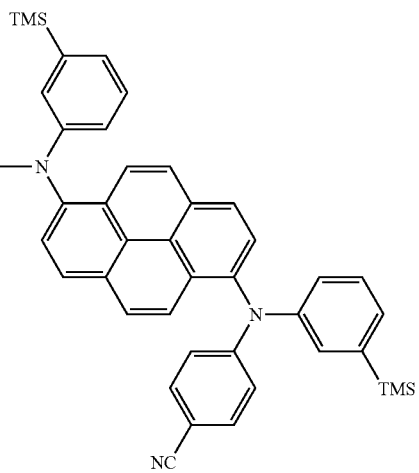
BD 55
BD 56
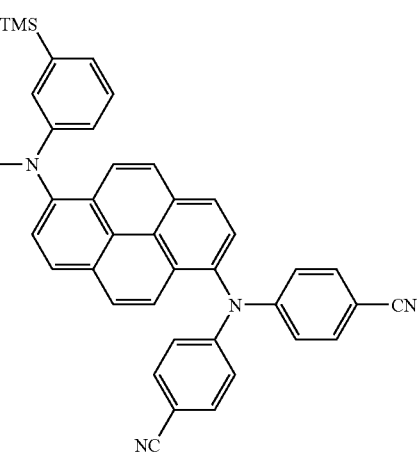

-continued
BD 57
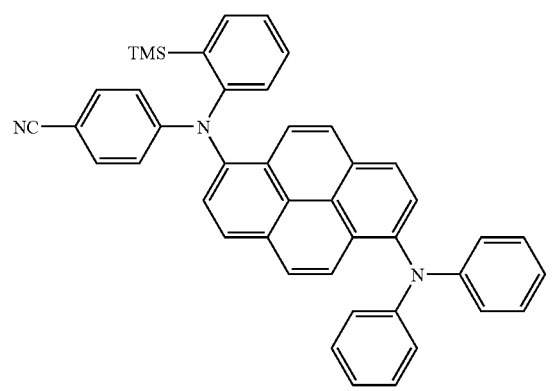
BD 58
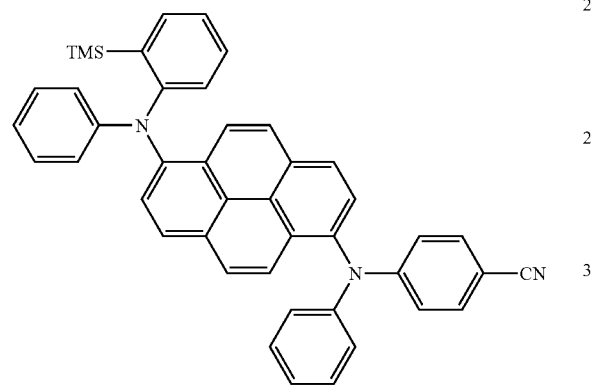
BD 59
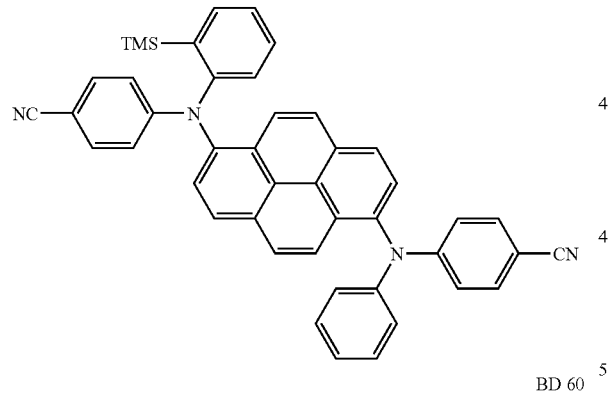
BD 60
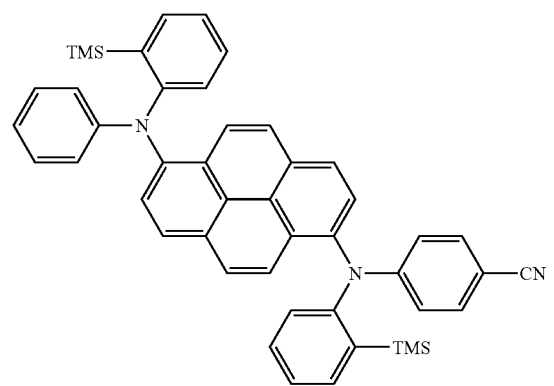
-continued
BD 61
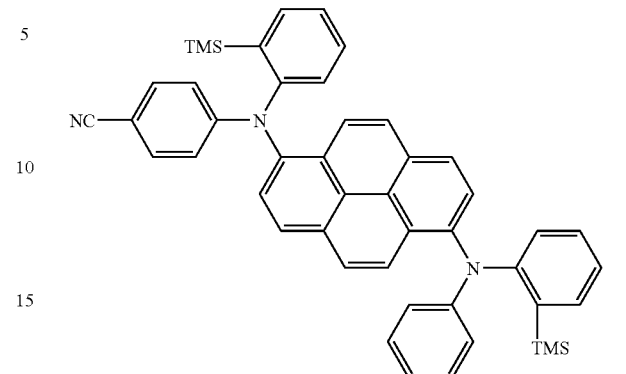
BD 62
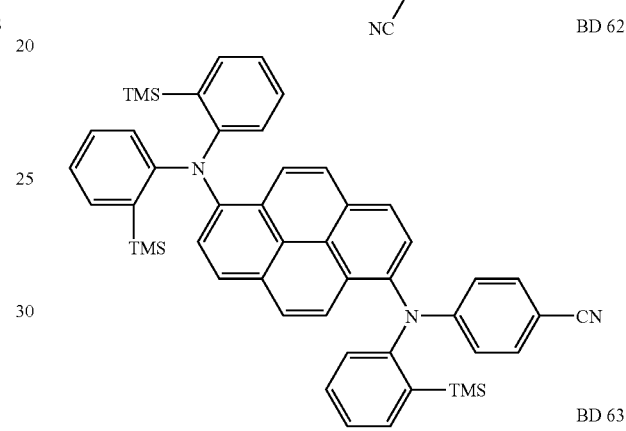
BD 63
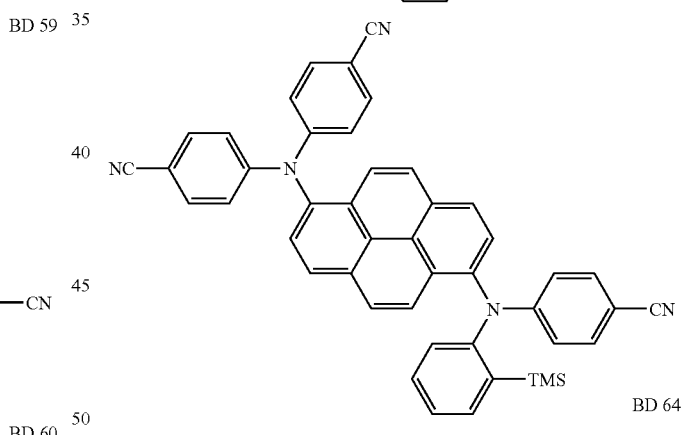
BD 64
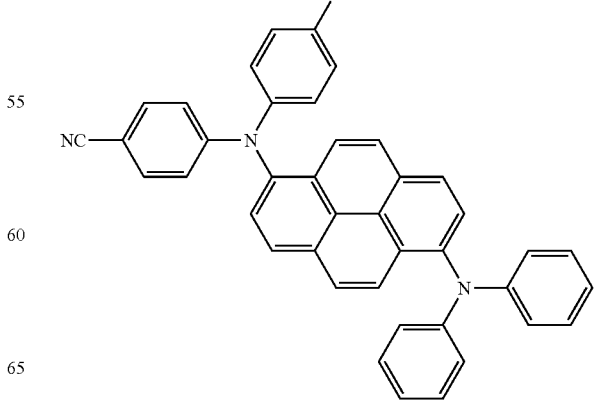

-continued
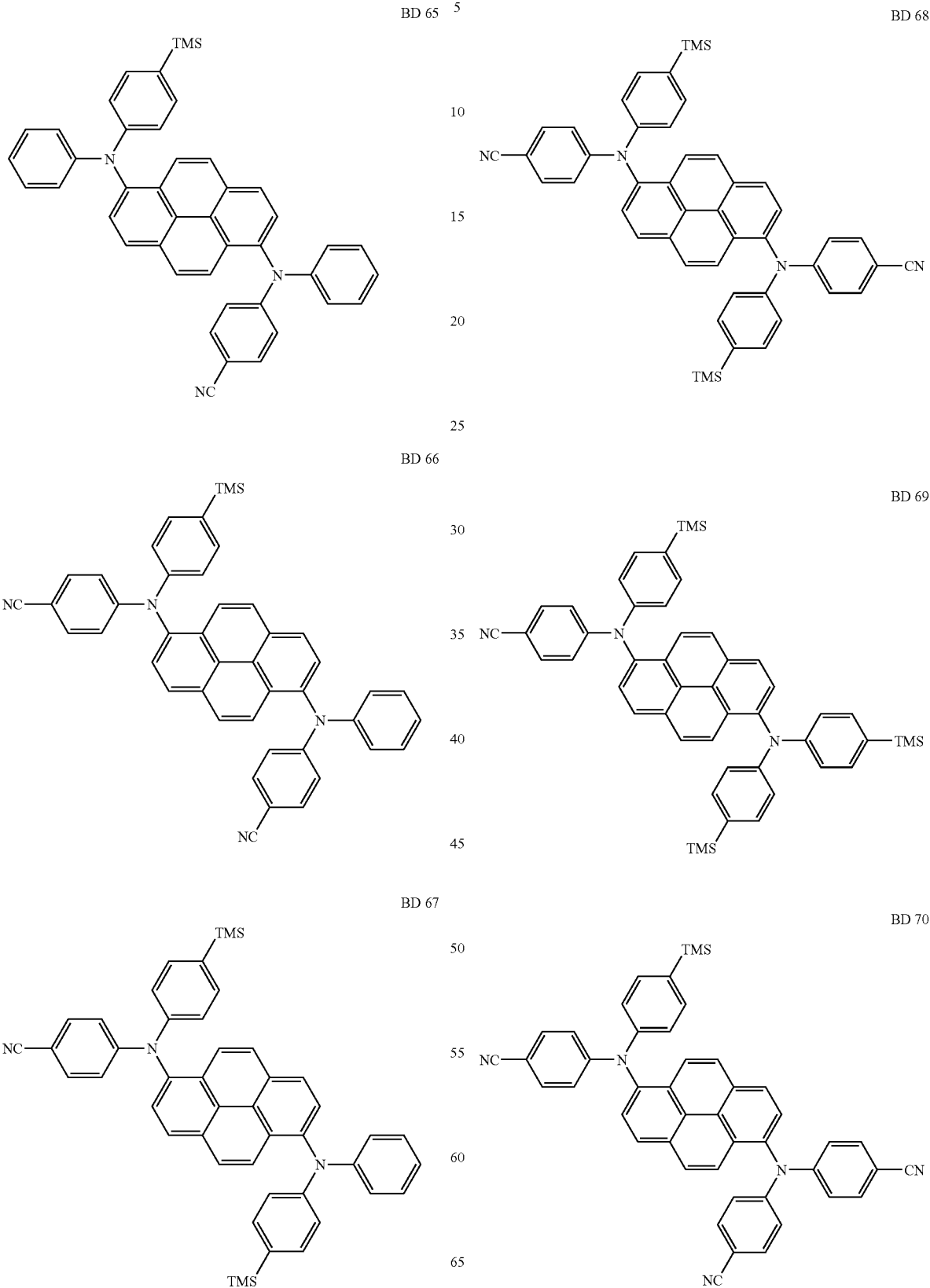

-continued
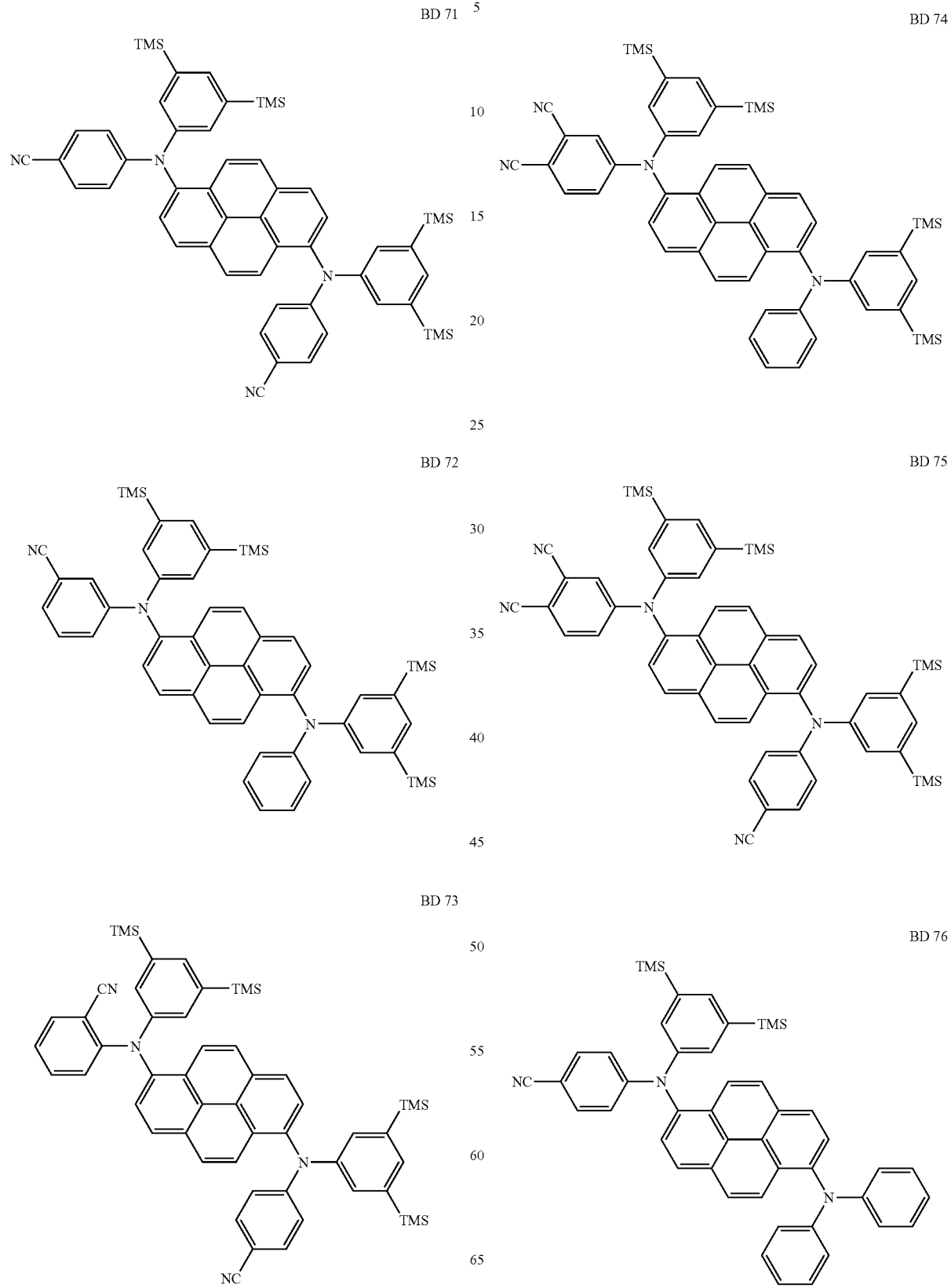

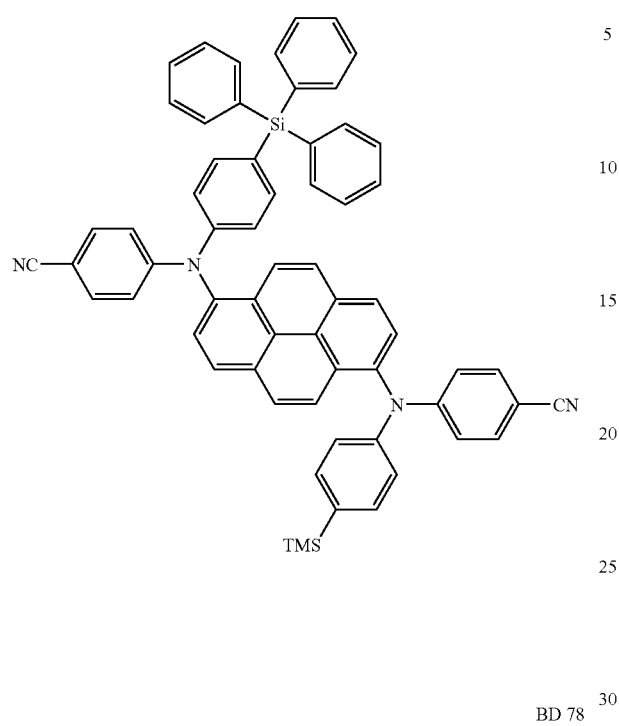

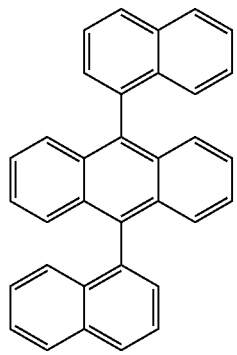

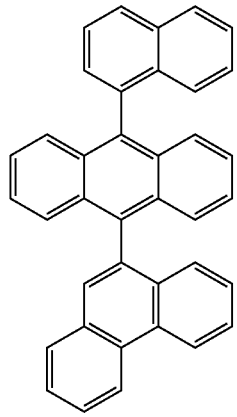

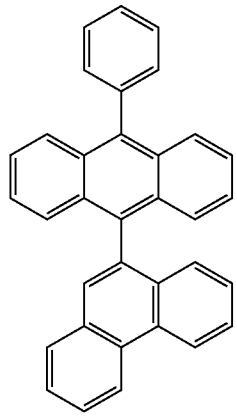

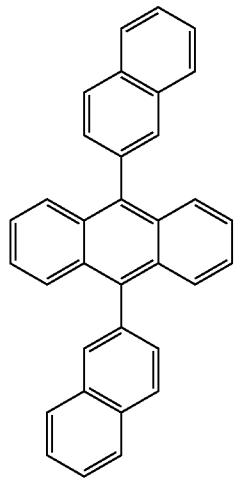

wherein TMS denotes trimethylsilyl.

In another aspect, the present invention provides an organic electroluminescent device comprising an anode, an organic light-emitting layer and a cathode wherein the organic light-emitting layer includes the blue light-emitting compound represented by Formula 1.

In a preferred embodiment, the organic light-emitting layer may further include an anthracene host compound selected from the following compounds:

-continued

BH-5
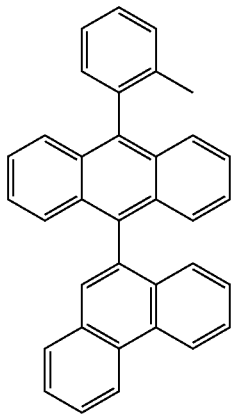

BH-6
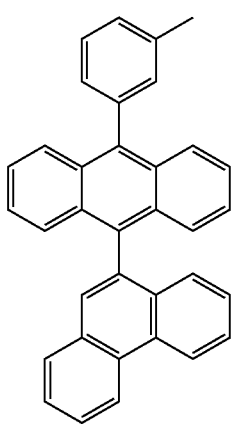

BH-7
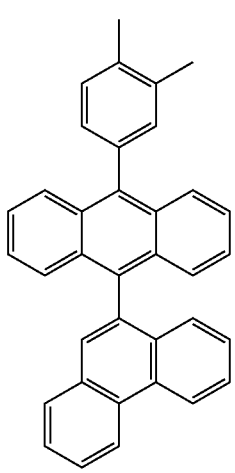

-continued

BH-8
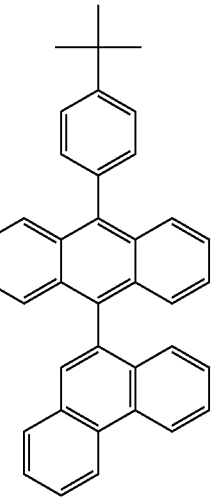

BH-9
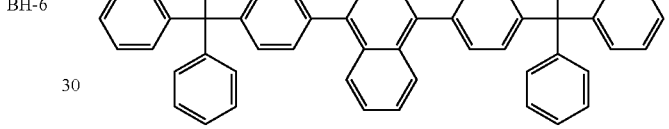

In a further preferred embodiment, the organic electroluminescent device may further comprise a hole transport layer disposed between the anode and the organic light-emitting layer, and an electron transport layer disposed between the cathode and the organic light-emitting layer.

In a still further preferred embodiment, the organic electroluminescent device may further comprise a hole injecting layer disposed under the hole transport layer.

In another preferred embodiment, the organic electroluminescent device may further comprise an electron injecting layer disposed on the electron transport layer.

Preferably, the hole transport layer may be formed of N,N'-bis(3-methylphenyl)-N,N'-diphenyl-[1,1'-biphenyl]-4,4'-diamine (TPD) or N,N'-di(naphthalen-1-yl)-N,N'-diphenylbenzidine (α-NPD).

Also preferably, the hole injecting layer may be formed of copper phthalocyanine (CuPc), 4,4',4"-tri(N-carbazolyl)triphenylamine (TCTA), 4,4',4"-tris(3-methylphenylphenylamino)triphenylamine (m-MTDATA) or DAPEB.

BRIEF DESCRIPTION OF THE DRAWINGS

The above and other objects, features and other advantages of the present invention will be more clearly understood from the following detailed description taken in conjunction with the accompanying drawing, in which.

DETAILED DESCRIPTION OF THE PREFERRED EMBODIMENTS

Figure 1:
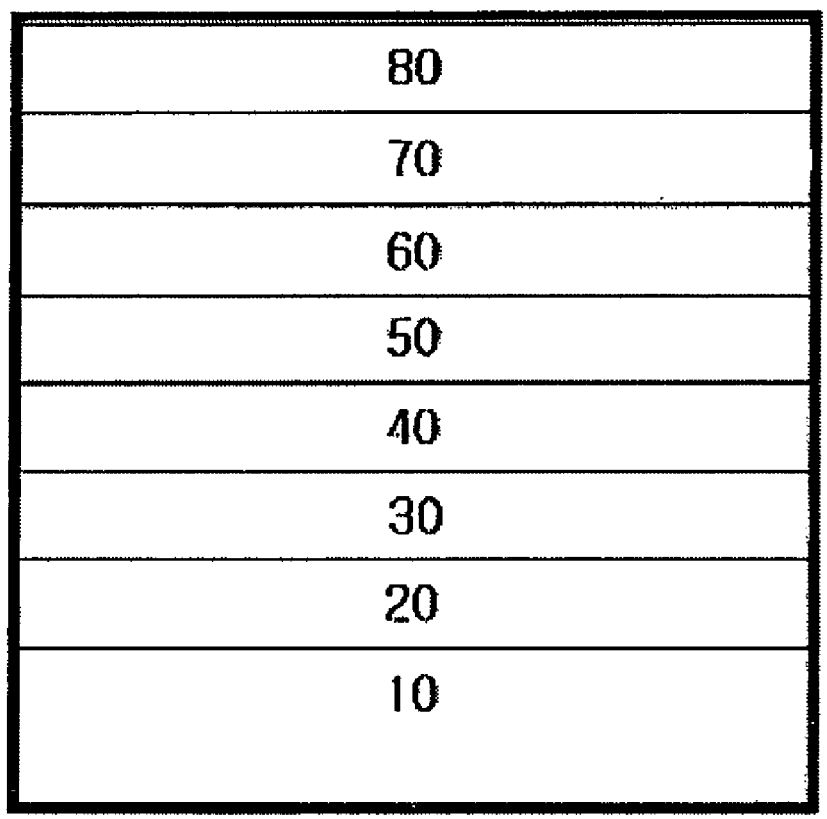
FIG. 1 is a schematic cross-sectional view of an organic electroluminescent device according to an embodiment of the present invention.

Reference will now be made in detail to the preferred embodiments of the present invention, examples of which are illustrated in the drawings attached hereinafter, wherein like reference numerals refer to like elements throughout.

The presence of at least one cyano group bonded to the corresponding phenyl group in the blue light-emitting compound (i.e. pyrene derivative) of the present invention enables the use of the blue light-emitting compound in the fabrication of an organic electroluminescent device with improved color purity. In addition, the presence of at least one alkylsilyl or arylsilyl group in the blue light-emitting compound of the present invention enables the use of the blue light-emitting compound in the fabrication of an organic electroluminescent device with improved life characteristics. Generally, the introduction of various highly electronegative electron-withdrawing groups to a compound results in improved color purity but causes greatly decreased efficiency, thus making the compound not suitable as a blue light-emitting compound.

In contrast, the use of the blue light-emitting compound according to the present invention improves the color purity of an organic electroluminescent device while maintaining the efficiency of the organic electroluminescent device. In addition, the function of the alkylsilyl or arylsilyl group present in the blue light-emitting compound of the present invention advantageously contributes to improvement in the life characteristics of an organic electroluminescent device.

The organic electroluminescent device of the present invention comprises an organic light-emitting layer, an anode and a cathode wherein the organic light-emitting layer includes the blue light-emitting compound represented by Formula 1. Since the organic electroluminescent device of the present invention has improved color purity, it can be used to fabricate a full-color display. Another advantage of the organic electroluminescent device according to the present invention is long lifetime.

The organic light-emitting layer may further include an anthracene host compound selected from the following compounds.

BH-1

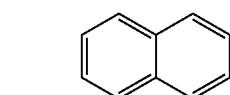

BH-2

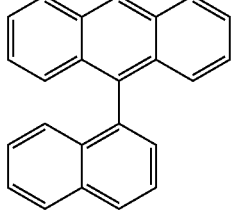

BH-3

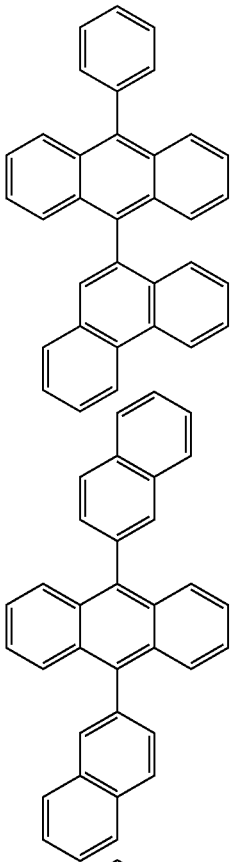

BH-4

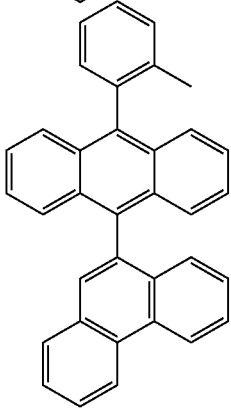

BH-5

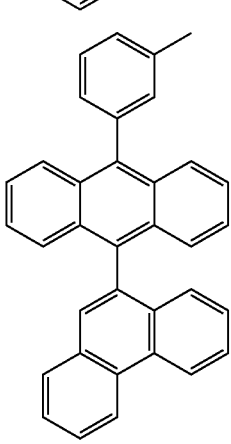

BH-6

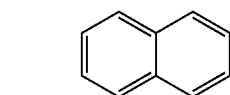
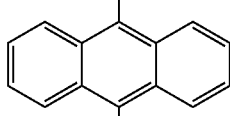
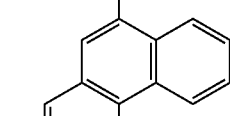
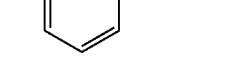

-continued

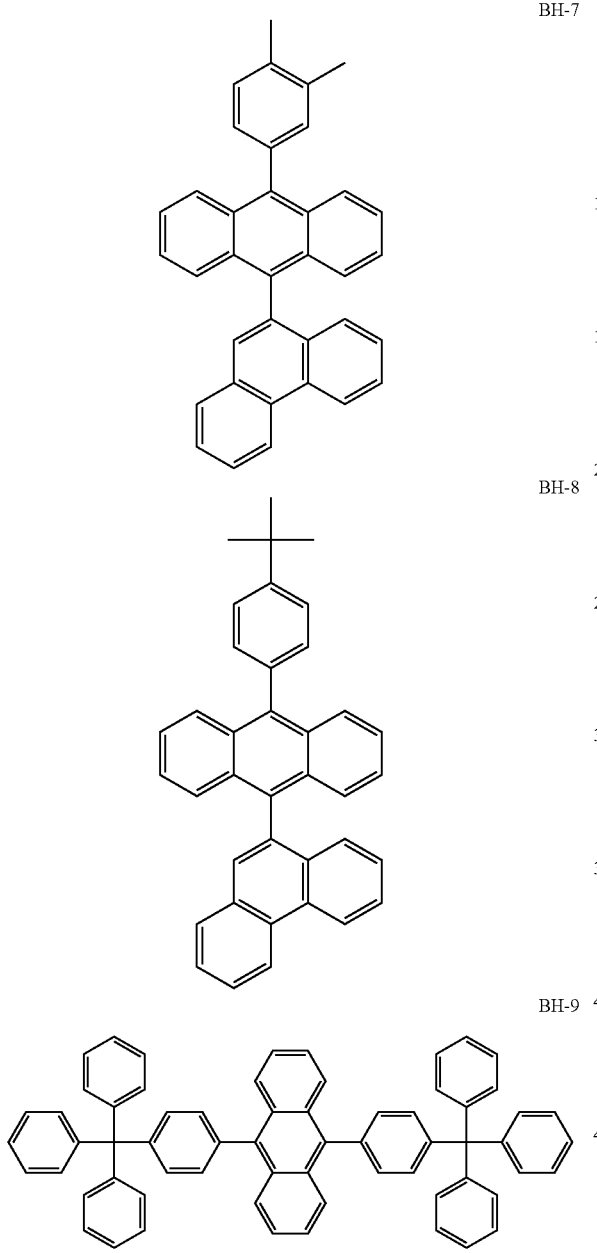

BH-7

BH-8

BH-9

In this case, the pyrene derivative of the present invention functions as a guest material and the anthracene compound functions as a host material. Specifically, the light absorption of the anthracene compound occurs in a shorter wavelength range than that of the pyrene derivative, and the peak absorption wavelength of the anthracene compound is almost consistent with the absorption wavelength of the pyrene derivative. Accordingly, when both the anthracene compound and the pyrene derivative are present within the organic light-emitting layer, the host material returns to the ground state without its own light emission while transferring excitation energy to the guest material.

In addition, since only the guest material in the excitation state emits the excitation energy as blue light, the luminescence efficiency of blue emission is improved. Generally, in the case where light-emitting molecules are used alone to form a thin film or are present at a high concentration within a thin film, they are in close proximity to each other, thus causing the occurrence of interactions therebetween and deterioration in luminescence efficiency due to concentration quenching.

In contrast, the combined use of the guest compound and the host compound to form the organic light-emitting layer of the organic electroluminescent device according to the present invention allows the guest molecules to be dispersed at a relatively low concentration, thus effectively inhibiting the occurrence of concentration quenching.

The organic electroluminescent device of the present invention may further comprise a hole transport layer (HTL) disposed between the anode and the organic light-emitting layer, and an electron transport layer (ETL) disposed between the cathode and the organic light-emitting layer.

The hole transport layer is formed to facilitate the injection of holes from the anode. As an exemplary material for the hole transport layer, an electron-donating compound having a low ionization potential is used. Examples of widely used electron-donating compounds include diamine, triamine and tetraamine derivatives having triphenylamine as a basic skeleton. Any material that is commonly used in the art may be used to form the hole transport layer in the present invention, and examples thereof include, but are not limited to, N,N'-bis(3-methylphenyl)-N,N'-diphenyl-[1,1'-biphenyl]-4,4'-diamine (TPD) and N,N'-di(naphthalen-1-yl)-N,N'-diphenyl-benzidien (α-NPD), which are represented below:

HTL-1

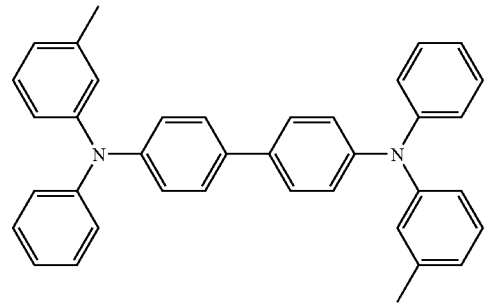

(TPD)

HTL-2

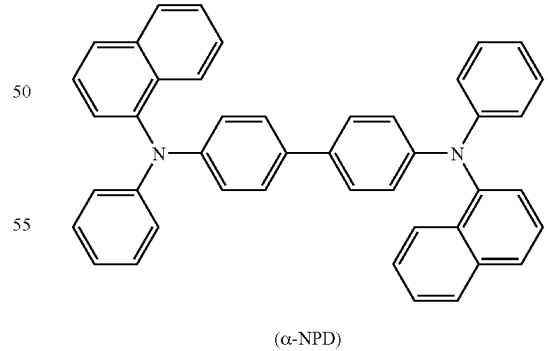

(α-NPD)

The organic electroluminescent device of the present invention may also further comprise a hole injecting layer (HIL) disposed under the hole transport layer. Any material that is commonly used in the art may be used without any particular limitation to form the hole injecting layer in the present invention. Suitable materials for the hole injecting layer include CuPc and starburst-type amines, e.g., TCTA, m-MTDATA and DAPEB, which are represented below:

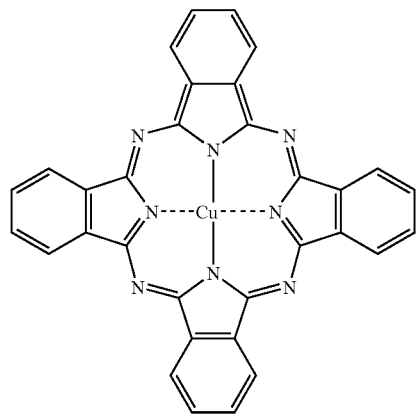

(CuPc) HIL-1

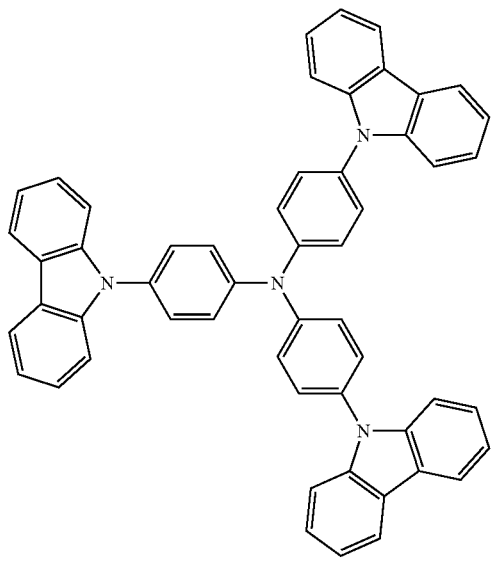

(TCTA) HIL-2

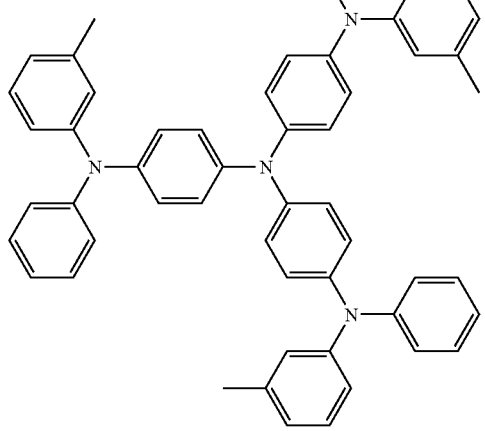

(m-MTDATA) HIL-3

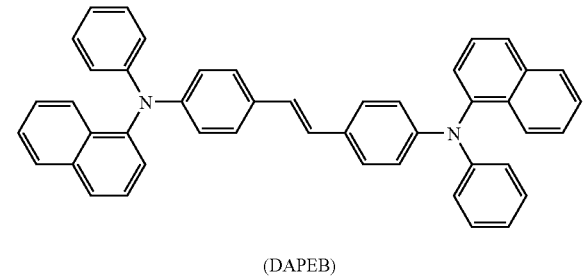

(DAPEB) HIL-4

The electron transport layer of the organic electroluminescent device according to the present invention serves to sufficiently transport electrons from the cathode to the organic light-emitting layer, and to inhibit the migration of unbound holes in the organic light-emitting layer, thereby increasing the opportunity for the unbound holes to recombine with the electrons in the light-emitting layer. It is to be understood that any material can be used without any particular limitation to form the electron transport layer so long as it is commonly used in the art. Examples of suitable materials for the electron transport layer include anthracene derivatives, pyrene derivatives and oxadiazole derivatives, such as PBD, BMD, BND and Alq$_3$, some of which are enumerated below:

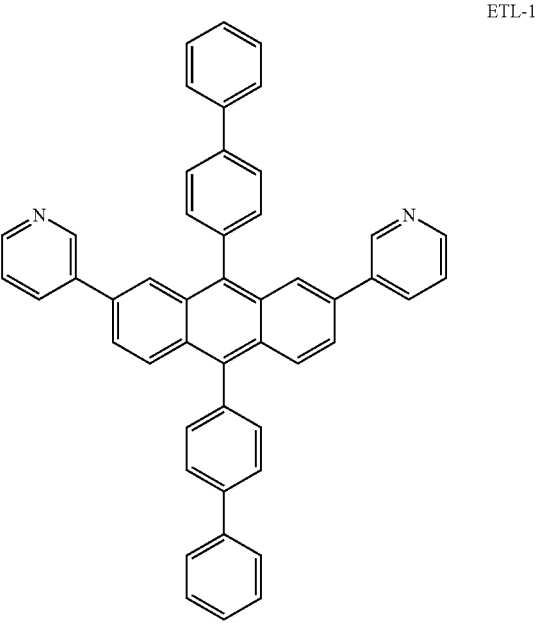

ETL-1

-continued

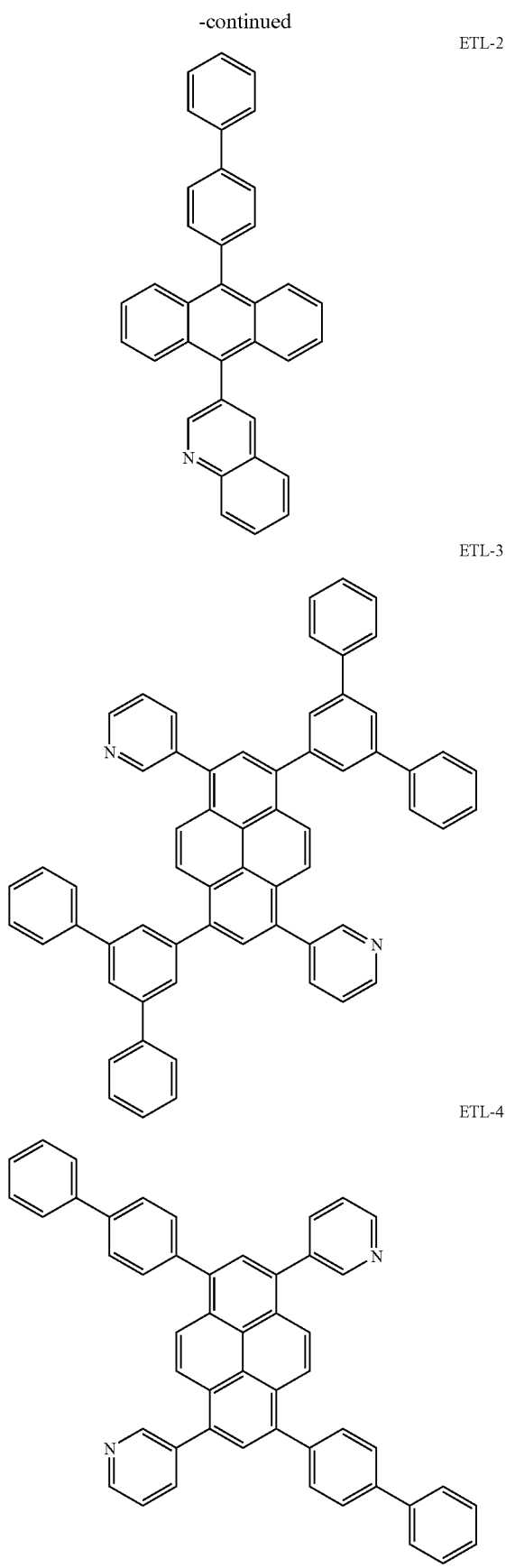

ETL-2

ETL-3

ETL-4

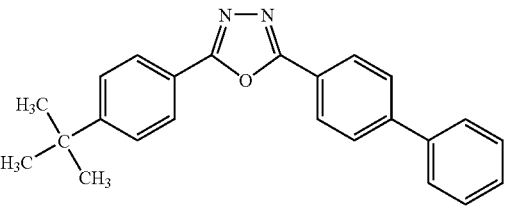

(PBD)

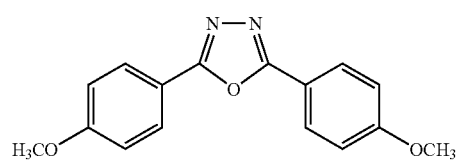

(BMD)

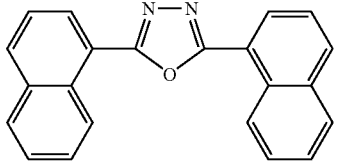

(BND)

ETL-5

ETL-6

ETL-7

In addition, the organic electroluminescent device of the present invention may further comprise an electron injecting layer (EIL) disposed on the electron transport layer to facilitate the injection of electrons from the cathode. The formation of the electron injecting layer contributes to an improvement in the power efficiency of the device. Any material that is commonly used in the art may be used to form the electron injecting layer in the present invention, and examples thereof include, but are not particularly limited to, LiF, NaCl, CsF, $Li_2O$ and BaO.

FIG. 1 is a cross-sectional view showing the structure of an organic electroluminescent device according to an embodiment of the present invention. The organic electroluminescent device of the present invention comprises an anode 20, a hole transport layer 40, an organic light-emitting layer 50, an electron transport layer 60, and a cathode 80. If necessary, the organic electroluminescent device may further comprise a hole injecting layer 30 and an electron injecting layer 70. In addition to the hole and electron injecting layers, the organic electroluminescent device may further comprise one or two intermediate layers. Also, the organic electroluminescent device may further comprise a hole blocking layer or an electron blocking layer.

With reference to FIG. 1, the organic electroluminescent device of the present invention and a fabrication method thereof will be explained below. First, an anode material is coated on a substrate 10 to form an anode 20. The substrate 10 may be any one used in conventional organic electroluminescent (EL) devices. An organic substrate or a transparent plastic substrate is preferred in terms of transparency, surface smoothness, ease of handling and waterproof qualities. As the anode material, a highly transparent and electrically conductive material is used, for example, indium tin oxide (ITO), indium zinc oxide (IZO), tin oxide ($SnO_2$) or zinc oxide (ZnO). A hole injecting material is deposited on the anode 20 by vacuum thermal evaporation or spin coating to form a hole injecting layer 30, and then a hole transport material is deposited on the hole injecting layer 30 by vacuum thermal evaporation or spin coating to form a hole transport layer 40. Subsequently, an organic light-emitting layer 50 is formed on the hole transport layer 40. If desired, a hole blocking layer (not shown) may be formed on the organic light-emitting layer 50 by vacuum deposition or spin coating. The hole blocking layer is formed of a material having a very low HOMO level to eliminate the problems, i.e. shortened lifetime and low efficiency of the device, which are encountered when holes enter the cathode through the organic light-emitting layer. The hole blocking material is not particularly limited; it must only have the ability to transport electrons and a higher ionization potential than the light-emitting compound. Representative hole blocking materials are BAlq, BCP and TPBI. An electron transport layer 60 is formed on the hole blocking layer by vacuum deposition or spin coating, and an electron injecting layer 70 is formed thereon. A cathode metal is deposited on the electron injecting layer 70 by vacuum thermal evaporation to form a cathode 80, completing the fabrication of the organic EL device. As the cathode metal, there may be used, for example, lithium (Li), magnesium (Mg), aluminum (Al), aluminum-lithium (Al—Li), calcium (Ca), magnesium-indium (Mg—In) or magnesium-silver (Mg—Ag). A light-transmissive cathode made of ITO or IZO may be used to fabricate a top emission device.

Hereinafter, the present invention will be explained in more detail with reference to the examples. However, these examples are not intended to limit the present invention.

Example 1

1(a): Synthesis of N-(4-cyanobenzo)-N'-(4-trimethylsilylbenzo)amine

4-Trimethylsilylbromobenzene (150 g, 0.65 moles) and 4-aminobenzonitrile (92.8 g, 0.79 moles) were dissolved in 2,500 ml of toluene in a three-neck round-bottom flask. To the solution were added palladium (II) acetate (5.9 g, 0.03 moles), 2,2'-bis(diphenylphosphino)-1,1'-binaphthyl (16.3 g, 0.03 moles) and sodium t-butoxide (94.4 g, 0.98 moles). The mixture was allowed to react for 48 hours while the temperature of the flask was raised to 85° C. After completion of the reaction, the hot reaction solution was filtered through a Buchner funnel containing a bed of celite. The filtrate was concentrated under reduced pressure at 50° C., and then the obtained concentrate was purified by column chromatography using hexane and ethyl acetate (4/1) as eluents. The developed solvents were completely removed to yield 56.9 g (0.21 moles, 32.6%) of the title product.

1(b): Synthesis of 1-[N-(4-cyanobenzo)-N'-(4-trimethylsilylbenzo)amino]pyrene (BD 01)

1-Bromopyrene (20 g, 0.07 moles) and N-(4-cyanobenzo)-N'-(4-trimethylsilylbenzo)amine (22.7 g, 0.08 moles) were dissolved in 400 ml of toluene in a three-neck round-bottom flask. To the solution were added palladium (II) acetate (0.63 g, 0.002 moles), 2,2'-bis(diphenylphosphino)-1,1'-binaphthyl (1.77 g, 0.002 moles) and sodium t-butoxide (13.6 g, 0.14 moles). The mixture was allowed to react for 48 hours while the temperature of the flask was raised to 90° C. After completion of the reaction, the hot reaction solution was filtered through a Buchner funnel containing a bed of celite. The filtrate was concentrated under reduced pressure at 50° C. to obtain a brown crystal, and then the brown crystal was purified by column chromatography using hexane and ethyl acetate (4/1) as eluents. The developed solvents were removed to yield 5.6 g (0.012 moles, 17%) of the title product as a solid.

$^1$H NMR (300 MHz, CDCl$_3$): δ 8.30-8.33 (d, 1H), 8.25-8.13 (m, 4H), 8.10-8.14 (d, 2H), 8.05-8.08 (d, 1H), 7.89-7.93 (d, 1H), 7.48-7.51 (d, 2H), 7.41-7.45 (d, 2H), 7.21-7.24 (d, 2H), 6.92-6.96 (d, 2H), 0.27 (s, 9H)

1(c): Fabrication of Organic Electroluminescent Device

An ITO-deposited glass substrate was patterned to have a light-emitting area of 3 mm×3 mm, followed by cleaning. After the substrate was mounted in a vacuum chamber, the pressure of the chamber was adjusted to 1×10$^{-6}$ torr. HIL-4 (DAPEB, 650 Å), HTL-2 (α-NPD, 400 Å), BD 01 (5%) synthesized in Example 1(b)+BH-1 (200 Å), ETL-1 (350 Å), LiF (5 Å) and Al (1,000 Å) were deposited in this order on the ITO to form respective films, completing the fabrication of an organic electroluminescent device.

Example 2

2(a): Synthesis of N-(4-triphenylsilylbenzo)-N'-(4-cyanobenzo)amine

4-Triphenylsilylbromobenzene (30 g, 0.072 moles) and 4-aminobenzonitrile (10.2 g, 0.086 moles) were dissolved in 600 ml of toluene in a three-neck round-bottom flask. To the solution were added palladium (II) acetate (0.65 g, 0.003 moles), 2,2'-bis(diphenylphosphino)-1,1'-binaphthyl (1.8 g, 0.003 moles) and sodium t-butoxide (13.88 g, 0.144 moles). The mixture was allowed to react for 48 hours while the temperature of the flask was raised to 90° C. After completion of the reaction, the hot reaction solution was filtered through a Buchner funnel containing a bed of celite. The filtrate was concentrated under reduced pressure at 50° C., and then the obtained concentrate was purified by column chromatography using hexane and ethyl acetate (4/1) as eluents. The developed solvents were completely removed to yield 19.6 g of (0.04 moles, 60%) of the title product as a solid.

2(b): Synthesis of 1-[N-(4-triphenylsilylbenzo)-N'-(4-cyanobenzo)amino]pyrene (BD 07)

1-Bromopyrene (10 g, 0.035 moles) and N-(4-triphenylsilylbenzo-N'-(4-cyanobenzo)amine (19 g, 0.042 moles) were dissolved in 200 ml of toluene in a three-neck round-bottom flask. To the solution were added palladium (II) acetate (0.9 g, 0.004 moles), 2,2'-bis(diphenylphosphino)-1,1'-binaphthyl (2.57 g, 0.004 moles) and sodium t-butoxide (9.84 g, 0.07 moles). The mixture was allowed to react for 72 hours while the temperature of the flask was raised to 90° C. After completion of the reaction, the hot reaction solution was filtered through a Buchner funnel containing a bed of celite. The filtrate was concentrated under reduced pressure at 50° C. to obtain a brown crystal, and then the brown crystal was purified by column chromatography using hexane and ethyl acetate (4/1) as eluents. The developed solvents were removed to yield 4.6 g (0.007 moles, 20%) of the title product as a solid.

$^1$H NMR (300 MHz, CDCl$_3$): δ 8.25-8.28 (d, 1H), 8.22-8.10 (m, 4H), 8.08-8.12 (d, 2H), 8.03-8.06 (d, 1H), 7.90-7.93 (d, 1H), 7.47-7.81 (m, 17H), 7.41-7.45 (d, 2H), 7.21-7.24 (d, 2H), 6.92-6.96 (d, 2H)

2(c): Fabrication of Organic Electroluminescent Device

An ITO-deposited glass substrate was patterned to have a light-emitting area of 3 mm×3 mm, followed by cleaning. After the substrate was mounted in a vacuum chamber, the pressure of the chamber was adjusted to $1\times10^{-6}$ torr. HIL-4 (DAPEB, 650 Å), HTL-2 (α-NPD, 400 Å), BD 07 (5%) synthesized in Example 2(b)+BH-2 (200 Å), ETL-2 (350 Å), LiF (5 Å) and Al (1,000 Å) were deposited in this order on the ITO to form respective films, completing the fabrication of an organic electroluminescent device.

Example 3

3(a): Synthesis of N-(3-cyanobenzo)-N'-(4-trimethylsilylbenzo)amine

4-Trimethylsilylbromobenzene (40 g, 0.17 moles) and 3-aminobenzonitrile (24.7 g, 0.21 moles) were dissolved in 800 ml of toluene in a three-neck round-bottom flask. To the solution were added palladium (II) acetate (0.8 g, 0.003 moles), 2,2'-bis(diphenylphosphino)-1,1'-binaphthyl (2.2 g, 0.003 moles) and sodium t-butoxide (33.5 g, 0.35 moles). The mixture was allowed to react for 80 hours while the temperature of the flask was raised to 90° C. After completion of the reaction, the hot reaction solution was filtered through a Buchner funnel containing a bed of celite. The filtrate was concentrated under reduced pressure at 50° C., and then the obtained concentrate was purified by column chromatography using hexane and ethyl acetate (4/1) as eluents. The developed solvents were completely removed to yield 15.4 g (0.06 moles, 33.1%) of the title product as a liquid.

3(b): Synthesis of 1,6-di[N-(3-cyanobenzo)-N'-(4-trimethylsilylbenzo)amino]pyrene (BD 27)

1,6-Dibromopyrene (8.5 g, 0.024 moles) and N-(3-cyanobenzene)-N'-(4-trimethylsilylbenzo)amine (15.4 g, 0.057 moles) were dissolved in 300 ml of toluene in a three-neck round-bottom flask. To the solution were added palladium (II) acetate (0.2 g, 0.001 moles), 2,2'-bis(diphenylphosphino)-1,1'-binaphthyl (0.6 g, 0.001 moles) and sodium t-butoxide (9.1 g, 0.09 moles). The mixture was allowed to react for 48 hours while the temperature of the flask was raised to 90° C. After completion of the reaction, the hot reaction solution was filtered through a Buchner funnel containing a bed of celite. The filtrate was concentrated under reduced pressure at 50° C., and then the obtained concentrate was purified by column chromatography using hexane and ethyl acetate (4/1) as eluents. The developed solvents were removed to yield 2.7 g (0.005 moles, 19.5%) of the title product as a yellow crystal.

$^1$H NMR (300 MHz, CDCl$_3$): δ 8.18-8.21 (d, 2H), 8.08-8.12 (d, 2H), 7.98-8.02 (d, 2H), 7.83-7.87 (d, 2H), 7.41-7.45 (d, 4H), 7.12-7.24 (m, 12H), 0.27 (s, 18H)

3(c): Fabrication of Organic Electroluminescent Device

An ITO-deposited glass substrate was patterned to have a light-emitting area of 3 mm×3 mm, followed by cleaning. After the substrate was mounted in a vacuum chamber, the pressure of the chamber was adjusted to $1\times10^{-6}$ torr. HIL-4 (DAPEB, 650 Å), HTL-2 (α-NPD, 400 Å), BD 27 (5%) synthesized in Example 3(b)+BH-3 (200 Å), ETL-3 (350 Å), LiF (5 Å) and Al (1,000 Å) were deposited in this order on the ITO to form respective films, completing the fabrication of an organic electroluminescent device.

Example 4

4(a): Synthesis of N,N'-di(2-trimethylsilylbenzo)amine

2-Trimethylsilylbromobenzene (50 g, 0.218 moles) and 2-trimethylsilylbenzoamine (43.2 g, 0.262 moles) were dissolved in 500 ml of toluene in a three-neck round-bottom flask. To the solution were added palladium (II) acetate (0.98 g, 0.004 moles), 2,2'-bis(diphenylphosphino)-1,1'-binaphthyl (2.7 g, 0.004 moles) and sodium t-butoxide (42 g, 0.43 moles). The mixture was allowed to react for 24 hours while the temperature of the flask was raised to 90° C. After completion of the reaction, the hot reaction solution was filtered through a Buchner funnel containing a bed of celite. The filtrate was concentrated under reduced pressure at 50° C. to obtain a crystal. The crystal was dissolved in 2 L of dichloromethane, and then the dichloromethane solution was subjected to phase separation using water. The organic layer was dried over anhydrous magnesium sulfate and concentrated under reduced pressure to obtain a crystal. The crystal was purified by column chromatography using dichloromethane as an eluent. The dichloromethane extract was concentrated to remove the eluent, mixed with a small amount of methanol to wash the concentrate, and filtered to yield 30.5 g (0.098 moles, 45%) of the title product as a crystal.

4(b): Synthesis of N-(2-trimethylsilylbenzo-N'-(2-cyanobenzo)amine

2-Trimethylsilylbromobenzene (40 g, 0.17 moles) and 2-cyanobenzoamine (24.7 g, 0.21 moles) were dissolved in 500 ml of toluene in a three-neck round-bottom flask. To the solution were added palladium (II) acetate (0.8 g, 0.003 moles), 2,2'-bis(diphenylphosphino)-1,1'-binaphthyl (2.2 g, 0.003 moles) and sodium t-butoxide (33.5 g, 0.35 moles). The mixture was allowed to react for 80 hours while the temperature of the flask was raised to 90° C. After completion of the reaction, the hot reaction solution was filtered through a Buchner funnel containing a bed of celite. The filtrate was concentrated under reduced pressure at 50° C., and then the obtained concentrate was purified by column chromatography using hexane and ethyl acetate (4/1) as eluents. The developed solvents were completely removed to yield 22.3 g (0.083 moles, 48%) of the title product.

4(c): Synthesis of 1-[N,N'-di(2-trimethylsilylbenzo)amino]-6-bromopyrene 1,6-Dibromopyrene (30 g, 0.083 moles) and N,N'-di(2-trimethylsilylbenzo)amine (31.3 g, 0.1 moles) were dissolved in 600 ml of toluene in a three-neck round-bottom flask. To the solution were added palladium (II) acetate (0.74 g, 0.004 moles), 2,2'-bis(diphenylphosphino)-1,1'-binaphthyl (2.07 g, 0.004 moles) and sodium t-butoxide (16 g, 0.16 moles). The mixture was allowed to react for 48 hours while the temperature of the flask was raised to 90° C. After completion of the reaction, the hot reaction solution was filtered through a Buchner funnel containing a bed of celite. The filtrate was concentrated under reduced pressure at 50° C., and then the concentrate was purified by column chromatography using hexane and ethyl acetate (4/1) as eluents. The developed solvents were removed to obtain a yellow crystal. The crystal was dissolved in dichloromethane to prepare a supersaturated solution of the crystal. A small amount of petroleum ether was added to the supersaturated solution to give 17.2 g (0.029, moles, 35%) of the title product as a crystal.

4(d): Synthesis of 1-[N,N'-di(2-trimethylsilylbenzo)amino]-6-[N-(2-trimethylsilylbenzo)-N'-(2-cyanobenzo)amino]pyrene (BD 41)

1-(N,N'-di(2-trimethylsilylbenzo)amino)-6-bromopyrene (15 g, 0.025 moles) and N-(2-trimethylsilylbenzo)-N'-(2-cyanobenzo)amine (8.9 g, 0.03 moles) were dissolved in 300 ml of toluene in a three-neck round-bottom flask. To the solution were added palladium (II) acetate (0.22 g, 0.001 moles), 2,2'-bis(diphenylphosphino)-1,1'-binaphthyl (0.63 g, 0.001 moles) and sodium t-butoxide (4.8 g, 0.05 moles). The mixture was allowed to react for 72 hours while the temperature of the flask was raised to 90° C. After completion of the reaction, the hot reaction solution was filtered through a Buchner funnel containing a bed of celite. The filtrate was concentrated under reduced pressure at 50° C. to obtain a brown crystal. The brown crystal was washed with acetone, dissolved in tetrahydrofuran, treated with charcoal, and concentrated under reduced pressure to prepare a supersaturated solution. An excess of acetone was added to the supersaturated solution to obtain a crystal. The crystal was filtered to give 2.9 g of the title product (0.004 moles, 15%) as a solid.

$^1$H NMR (300 MHz, CDCl$_3$): δ 8.15-8.18 (d, 2H), 8.05-8.07 (d, 2H), 8.01-8.04 (d, 2H), 7.76-7.80 (d, 2H), 7.40-7.48 (m, 4H), 7.31-7.37 (m, 4H), 7.21-7.28 (m, 4H), 6.90-6.98 (m, 4H), 0.27 (s, 27H).

4(e): Fabrication of Organic Electroluminescent Device

An ITO-deposited glass substrate was patterned to have a light-emitting area of 3 mm×3 mm, followed by cleaning. After the substrate was mounted in a vacuum chamber, the pressure of the chamber was adjusted to 1×10$^{-6}$ torr. HIL-4 (DAPEB, 650 Å), HTL-2 (α-NPD, 400 Å), BD 41 (5%) synthesized in Example 4(d)+BH-1 (200 Å), ETL-1 (350 Å), LiF (5 Å) and Al (1,000 Å) were deposited in this order on the ITO to form respective films, completing the fabrication of an organic electroluminescent device.

Example 5

5(a): Synthesis of 4-trimethylsilyl-1-bromobenzene 1,4-Dibromobenzene (500 g, 2.12 moles) was dissolved in THF (3.5 L) in a four-neck round-bottom flask. The flask was cooled to −78° C., and then 1.6M n-BuLi (1,600 ml, 2.56, moles) was rapidly added dropwise thereto. At the same temperature, the mixture was allowed to react for 2 hours. Thereafter, chlorotrimethylsilane (362 ml, 2.86 moles) was slowly added dropwise to the reaction mixture. The resulting mixture was reacted for 5 hours while warming to room temperature. After completion of the reaction, a mixture of triethylamine (100 ml) and methanol (200 ml) was added to the reaction mixture. The resulting mixture was stirred for one hour to obtain a crystal. The crystal was filtered, and then the filtrate was concentrated under reduced pressure at 60° C. to obtain a crystal.

The crystal was filtered off and the filtrate was diluted with dichloromethane. The dichloromethane solution was subjected to phase separation using water. The organic layer was dried over anhydrous magnesium sulfate and concentrated under reduced pressure at 60° C. The concentrate in the form of liquid organic matter was distilled to yield 230 g (1 mole, 47%) of the pure title product.

5(h): Synthesis of N-(4-cyanobenzo)-N'-(4-trimethylsilylbenzo)amine

4-Trimethylsilylbromobenzene (150 g, 0.65 moles) and 4-aminobenzonitrile (92.8 g, 0.79 moles) were dissolved in 2,500 ml of toluene in a three-neck round-bottom flask. To the solution were added palladium (II) acetate (5.9 g, 0.03 moles), 2,2'-bis(diphenylphosphino)-1,1'-binaphthyl (16.3 g, 0.03 moles) and sodium t-butoxide (94.4 g, 0.98 moles). The mixture was allowed to react for 48 hours while the temperature of the flask was raised to 85° C. After completion of the reaction, the hot reaction solution was filtered through a Buchner funnel containing a bed of celite. The filtrate was concentrated under reduced pressure at 50° C., and then the obtained concentrate was purified by column chromatography using hexane and ethyl acetate (4/1) as eluents. The developed solvents were completely removed to yield 56.9 g (0.21 moles, 32.6%) of the title product.

5(c): Synthesis of 1,6-di[N-(4-cyanobenzo)-N'-(4-trimethylsilylbenzo)amine]pyrene (BD 68)

1,6-Dibromopyrene (45 g, 0.125 moles) and N-(4-cyanobenzo)-N'-(4-trimethylsilylbenzo)amine (80 g, 0.3 moles) were dissolved in 1,000 ml of toluene in a three-neck round-bottom flask. To the solution were added palladium (II) acetate (1.1 g, 0.005 moles), 2,2'-bis(diphenylphosphino)-1, 1'-binaphthyl (3.1 g, 0.005 moles) and sodium t-butoxide (48 g, 0.5 moles). The mixture was allowed to react for 48 hours while the temperature of the flask was raised to 90° C. After completion of the reaction, the hot reaction solution was filtered through a Buchner funnel containing a bed of celite. The filtrate was concentrated under reduced pressure at 50° C. to obtain a brown crystal. The brown crystal was washed with acetone, dissolved in tetrahydrofuran, treated with charcoal, and concentrated under reduced pressure to prepare a supersaturated solution. An excess of acetone was added to the supersaturated solution to obtain a crystal. The crystal was filtered to give 43 g (0.06 moles, 47.1%) of the title product as a solid.

$^1$H NMR (300 MHz, CDCl$_3$): δ 8.20-8.23 (d, 2H), 8.08-8.12 (d, 2H), 8.01-8.04 (d, 2H), 7.86-7.90 (d, 2H), 7.45-7.48 (d, 4H), 7.41-7.45 (d, 4H), 7.21-7.24 (d, 4H), 6.92-6.96 (d, 4H), 0.27 (s, 18H)

5(d): Fabrication of Organic Electroluminescent Device

An ITO-deposited glass substrate was patterned to have a light-emitting area of 3 mm×3 mm, followed by cleaning. After the substrate was mounted in a vacuum chamber, the pressure of the chamber was adjusted to 1×10$^{-6}$ torr. HIL-4 (DAPEB, 650 Å), HTL-2 (α-NPD, 400 Å), BD 68 (5%) synthesized in Example 5(c)+BH-2 (200 Å), ETL-2 (350 Å), LiF (5 Å) and Al (1,000 Å) were deposited in this order on the ITO to form respective films, completing the fabrication of an organic electroluminescent device.

Example 6

6(a): Synthesis of N-[3,5-di(trimethylsilyl)]-N'-(4-cyanobenzo)amine 3,5-Di(trimethylsilyl)bromobenzene (50 g, 0.166 moles) and 4-aminobenzonitrile (23.5 g, 0.2 moles) were dissolved in 1,000 ml of toluene in a three-neck round-bottom flask. To the solution were added palladium (II) acetate (1.78 g, 0.008 moles), 2,2'-bis(diphenylphosphino)-1,1'-binaphthyl (4.95 g, 0.008 moles) and sodium t-butoxide (38.3 g, 0.4 moles). The mixture was allowed to react for 48 hours while the temperature of the flask was raised to 90° C. After completion of the reaction, the hot reaction solution was filtered through a Buchner funnel containing a bed of celite. The filtrate was concentrated under reduced pressure at 50° C., and then the obtained concentrate was purified by column chromatography using hexane and ethyl acetate (4/1) as eluents. The developed solvents were completely removed to yield 30.8 g (0.091 moles, 55%) of the title product as a solid.

6(b): Synthesis of 1,6-di[N-(3,5-di(trimethylsilyl))-N'-(4-cyanobenzo)amino]pyrene (BD 71)

1,6-Dibromopyrene (5 g, 0.0138 moles) and N-(3,5-di(trimethylsilyl))-N'-(4-cyanobenzo)amine (11.2 g, 0.033 moles) were dissolved in 200 ml of toluene in a three-neck round-bottom flask. To the solution were added palladium (II) acetate (0.12 g, 0.001 moles), 2,2'-bis(diphenylphosphino)-1,1'-binaphthyl (0.35 g, 0.001 moles) and sodium t-butoxide (2.7 g, 0.028 moles). The mixture was allowed to react for 72 hours while the temperature of the flask was raised to 90° C. After completion of the reaction, the hot reaction solution was filtered through a Buchner funnel containing a bed of celite. The filtrate was concentrated under reduced pressure at 50° C. to obtain a brown crystal. The brown crystal was washed with acetone, dissolved in tetrahydrofuran, treated with charcoal, and concentrated under reduced pressure to prepare a supersaturated solution. An excess of acetone was added to the supersaturated solution to obtain a crystal. The crystal was filtered to give 2.6 g (0.003 moles, 22%) of the title product as a solid.

$^1$H NMR (300 MHz, CDCl$_3$): δ 8.22-8.25 (d, 2H), 8.10-8.14 (d, 2H), 8.04-8.07 (d, 2H), 7.88-7.91 (d, 2H), 7.21-7.30 (m, 6H), 6.91-7.10 (m, 8H), 0.27 (s, 36H)

6(c): Fabrication of Organic Electroluminescent Device

An ITO-deposited glass substrate was patterned to have a light-emitting area of 3 mm×3 mm, followed by cleaning. After the substrate was mounted in a vacuum chamber, the pressure of the chamber was adjusted to 1×10$^{-6}$ torr. HIL-4 (DAPEB, 650 Å), HTL-2 (α-NPD, 400 Å), BD 71 (5%) synthesized in Example 6(b)+BH-3 (200 Å), ETL-3 (350 Å), LiF (5 Å) and Al (1,000 Å) were deposited in this order on the ITO to form respective films, completing the fabrication of an organic electroluminescent device.

Comparative Example 1

An ITO-deposited glass substrate was patterned to have a light-emitting area of 3 mm×3 mm, followed by cleaning. After the substrate was mounted in a vacuum chamber, the pressure of the chamber was adjusted to 1×10$^{-6}$ torr. HIL-4 (DAPEB, 650 Å), HTL-2 (α-NPD, 400 Å), the compound of Formula A (5%)+BH-1 (200 Å), Alq3 (350 Å), LiF (5 Å) and Al (1,000 Å) were deposited in this order on the ITO to form respective films, completing the fabrication of an organic electroluminescent device.

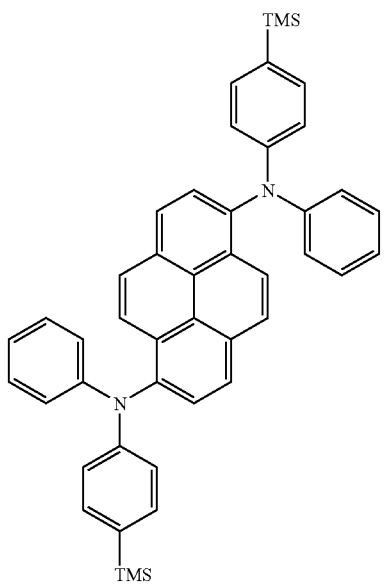

(A)

Comparative Example 2

An ITO-deposited glass substrate was patterned to have a light-emitting area of 3 mm×3 mm, followed by cleaning. After the substrate was mounted in a vacuum chamber, the pressure of the chamber was adjusted to 1×10$^{-6}$ torr. HIL-4 (DAPEB, 650 Å), HTL-2 (α-NPD, 400 Å), the compound of Formula B (5%)+BH-2 (200 Å), Alq3 (350 Å), LiF (5 Å) and Al (1,000 Å) were deposited in this order on the ITO to form respective films, completing the fabrication of an organic electroluminescent device.

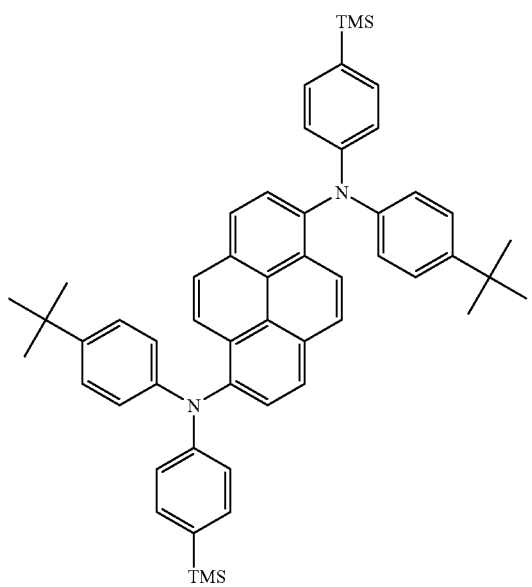

(B)

Comparative Example 3

An ITO-deposited glass substrate was patterned to have a light-emitting area of 3 mm×3 mm, followed by cleaning. After the substrate was mounted in a vacuum chamber, the pressure of the chamber was adjusted to 1×10$^{-6}$ torr. HIL-4

(DAPEB, 650 Å), HTL-2 (α-NPD, 400 Å), the compound of Formula C (5%)+BH-1 (200 Å), Alq3 (350 Å), LiF (5 Å) and Al (1,000 Å) were deposited in this order on the ITO to form respective films, completing the fabrication of an organic electroluminescent device.

(C)

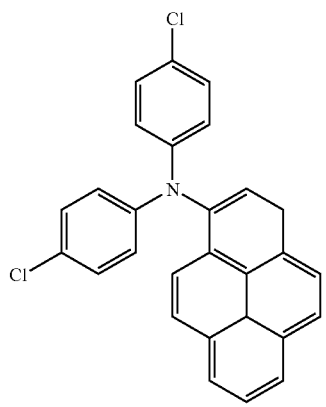

Comparative Example 4

An ITO-deposited glass substrate was patterned to have a light-emitting area of 3 mm×3 mm, followed by cleaning. After the substrate was mounted in a vacuum chamber, the pressure of the chamber was adjusted to $1\times10^{-6}$ torr. HIL-4 (DAPEB, 650 Å), HTL-2 (α-NPD, 400 Å), the compound of Formula D (5%)+BH-2 (200 Å), Alq3 (350 Å), LiF (5 Å) and Al (1,000 Å) were deposited in this order on the ITO to form respective films, completing the fabrication of an organic electroluminescent device.

(D)

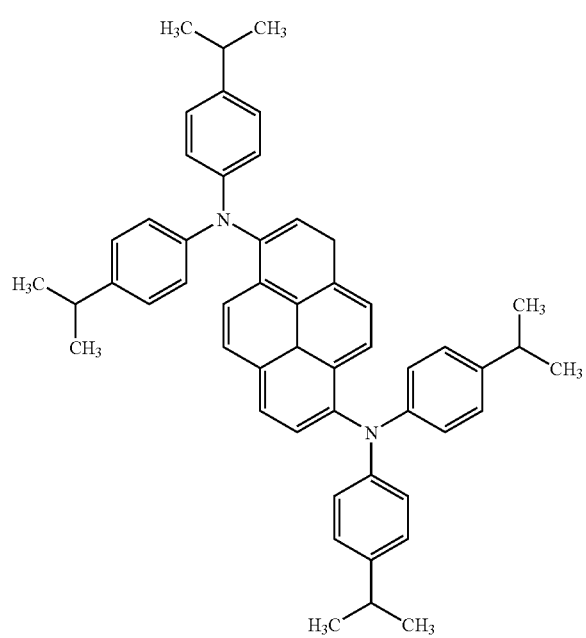

Comparative Example 5

An ITO-deposited glass substrate was patterned to have a light-emitting area of 3 mm×3 mm, followed by cleaning. After the substrate was mounted in a vacuum chamber, the pressure of the chamber was adjusted to $1\times10^{-6}$ torr. HIL-4 (DAPEB, 650 Å), HTL-2 (α-NPD, 400 Å), the compound of Formula E (5%)+BH-3 (200 Å), Alq3 (350 Å), LiF (5 Å) and Al (1,000 Å) were deposited in this order on the ITO to form respective films, completing the fabrication of an organic electroluminescent device.

(E)

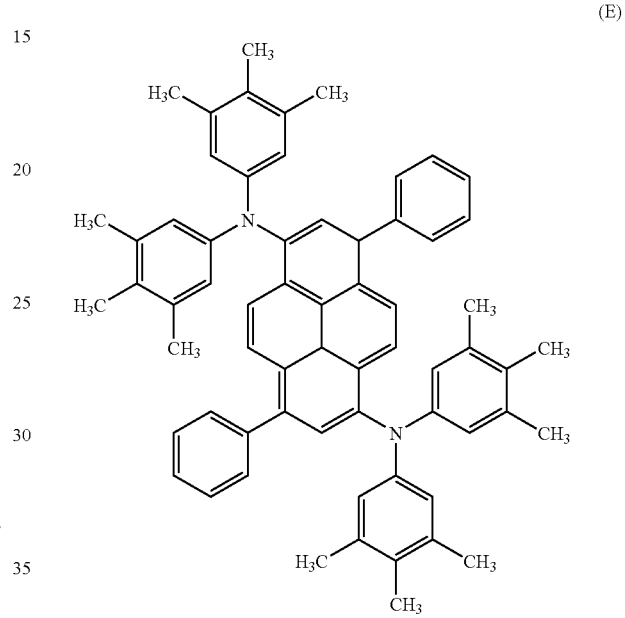

Test Example 1

The organic electroluminescent devices fabricated in Examples 1 to 6 and Comparative Examples 1 to 5 were tested for voltage, current, luminance, chromaticity coordinates and lifetime. The results are shown in Table 1. T80 indicates the time at which the luminance of each of the devices was decreased to 80% of the initial luminance.

TABLE 1

| Example No. | Voltage (V) | Current (mA) | Luminance (cd/m$^2$) | CIE (X) | CIE (Y) | T80 |
|---|---|---|---|---|---|---|
| Example 1 | 4.8 | 0.9 | 560 | 0.15 | 0.12 | 70 |
| Example 2 | 4.5 | 0.9 | 640 | 0.14 | 0.14 | 60 |
| Example 3 | 4.9 | 0.9 | 580 | 0.14 | 0.10 | 110 |
| Example 4 | 4.6 | 0.9 | 620 | 0.15 | 0.14 | 100 |
| Example 5 | 4.8 | 0.9 | 650 | 0.14 | 0.10 | 110 |
| Example 6 | 4.5 | 0.9 | 575 | 0.15 | 0.11 | 90 |
| Comparative Example 1 | 5.4 | 0.9 | 550 | 0.15 | 0.21 | 100 |
| Comparative Example 2 | 5.2 | 0.9 | 630 | 0.15 | 0.20 | 90 |
| Comparative Example 3 | 6.2 | 0.9 | 70 | 0.14 | 0.17 | 20 |
| Comparative Example 4 | 5.8 | 0.9 | 700 | 0.13 | 0.28 | 110 |
| Comparative Example 5 | 5.6 | 0.9 | 800 | 0.15 | 0.42 | 80 |

As shown in Table 1, the organic electroluminescent devices of the present invention showed improved color purity when compared to the devices using the respective conventional blue light-emitting compounds. In addition, the luminance of the devices according to the present invention was comparable or superior to that of the devices using the respective conventional blue light-emitting compounds. Furthermore, the life characteristics of the devices according to the present invention were superior to those of the devices using the respective conventional blue light-emitting compounds. Based on these advantages, the organic electroluminescent devices of the present invention can be suitably used to manufacture full-color displays. In contrast, the devices fabricated in Comparative Examples 1 to 2 showed high luminance and excellent life characteristics, but had the disadvantage of poor color purity. The device fabricated in Comparative Example 3 showed very low luminance and poor life characteristics. The devices fabricated in Comparative Examples 4 and 5 showed high luminance and excellent life characteristics, but had the disadvantage of poor color purity.

As apparent from the above description, the organic electroluminescent device of the present invention exhibits improved color purity of blue emission and excellent life characteristics without any decrease in luminance. Therefore, the organic electroluminescent device of the present invention can be suitably used to manufacture a full-color display.

The invention has been described in detail with reference to preferred embodiments thereof. However, it will be appreciated by those skilled in the art that changes may be made in these embodiments without departing from the principles and spirit of the invention, the scope of which is defined in the appended claims and their equivalents.

What is claimed is:

1. A blue light-emitting compound of Formula 1:

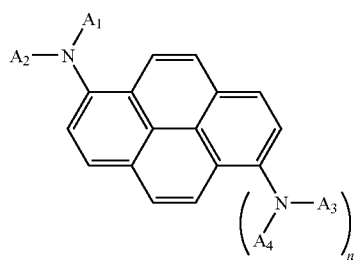

(1)

wherein $A_1$ to $A_4$ are each independently a $C_6$-$C_{20}$ aryl group which is unsubstituted or substituted with a group selected from the group consisting of $C_1$-$C_{10}$ alkyl, $C_1$-$C_{10}$ alkoxy, cyano, $C_1$-$C_{10}$ alkylamino, $C_1$-$C_{10}$ alkylsilyl, halogen, $C_6$-$C_{10}$ aryl, $C_6$-$C_{10}$ aryloxy, $C_6$-$C_{10}$ arylamino, $C_6$-$C_{10}$ arylsilyl and hydrogen, or a $C_4$-$C_{19}$ heteroaryl group containing at least one heteroatom selected from N, S and O atoms; if n is 0, the substituents of A1 and A2 include at least one cyano group and at least one alkylsilyl or arylsilyl group; and if n is 1, the substituents of A1 to A4 include at least one cyano group and at least one alkylsilyl or arylsilyl group.

2. The blue light-emitting compound according to claim 1, wherein the blue light-emitting compound is selected from the group consisting of the following compounds (2):

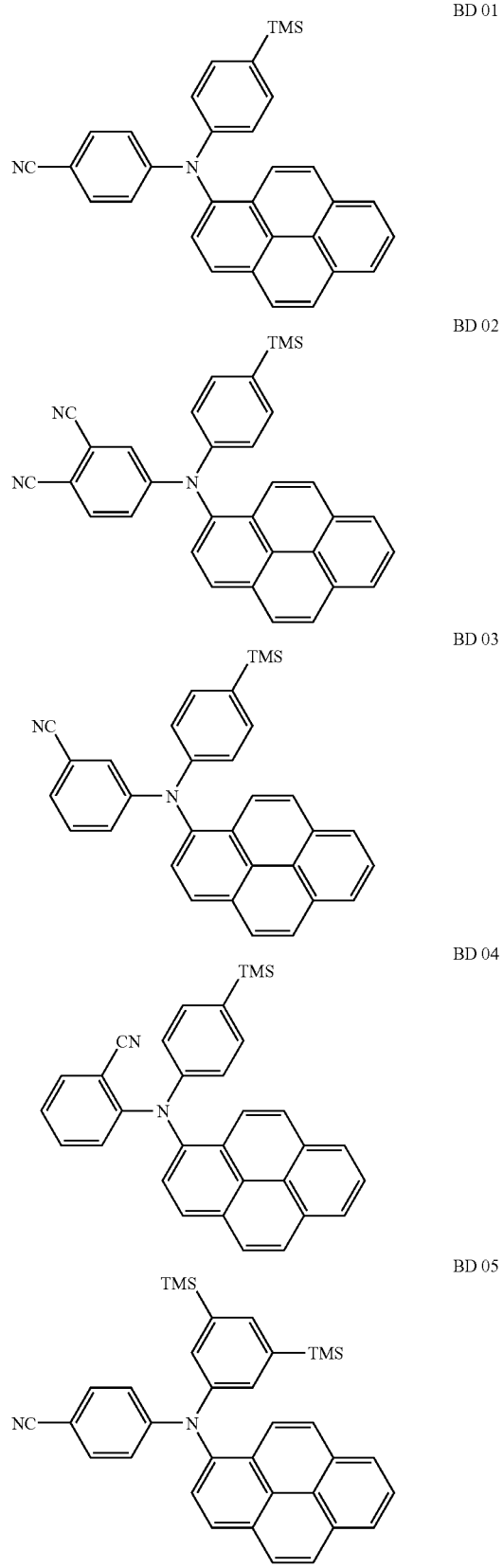

(2)

-continued
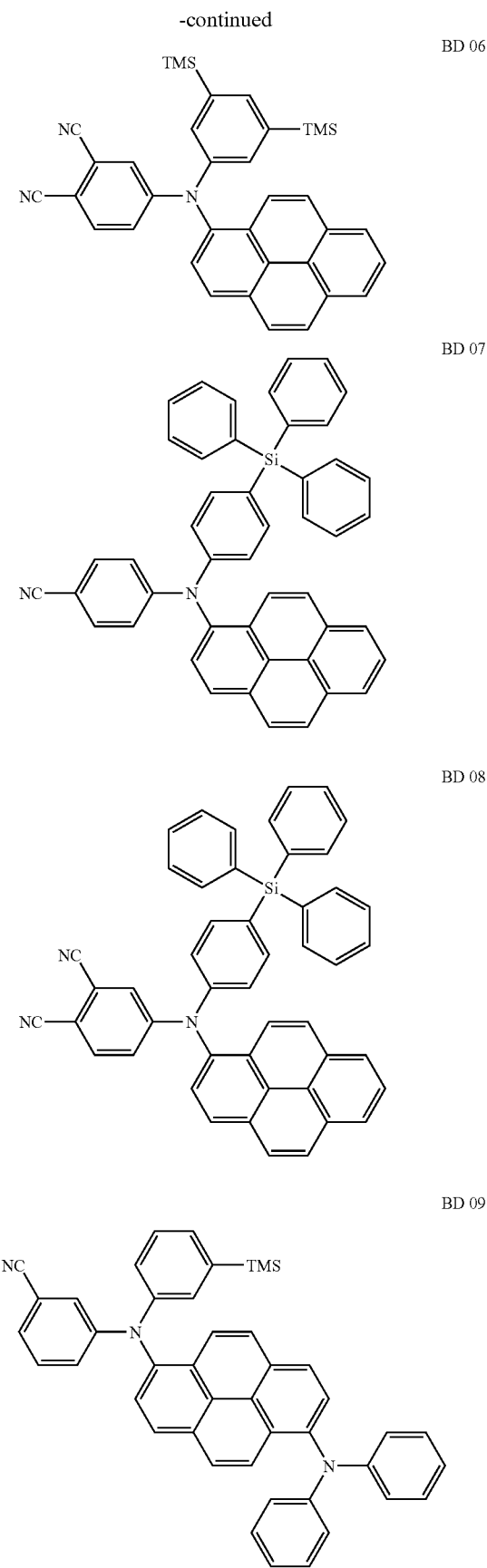
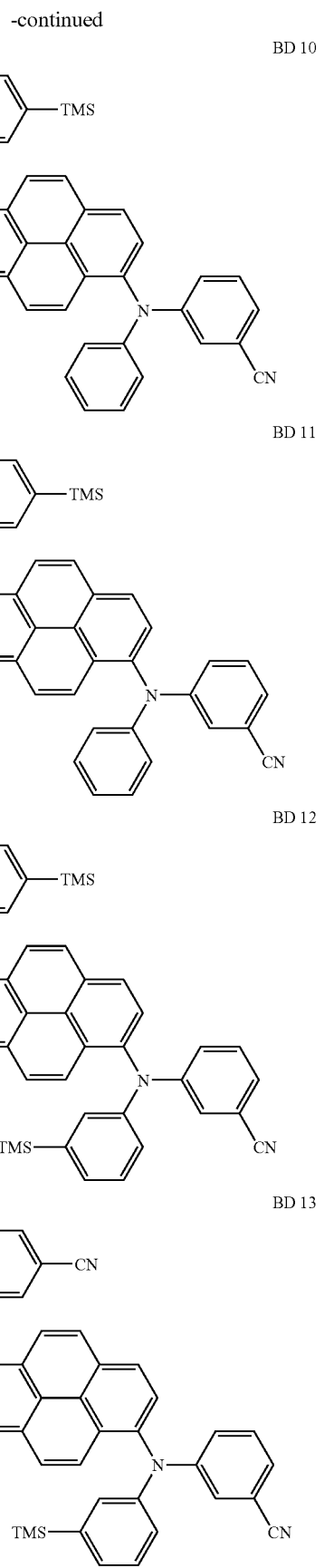

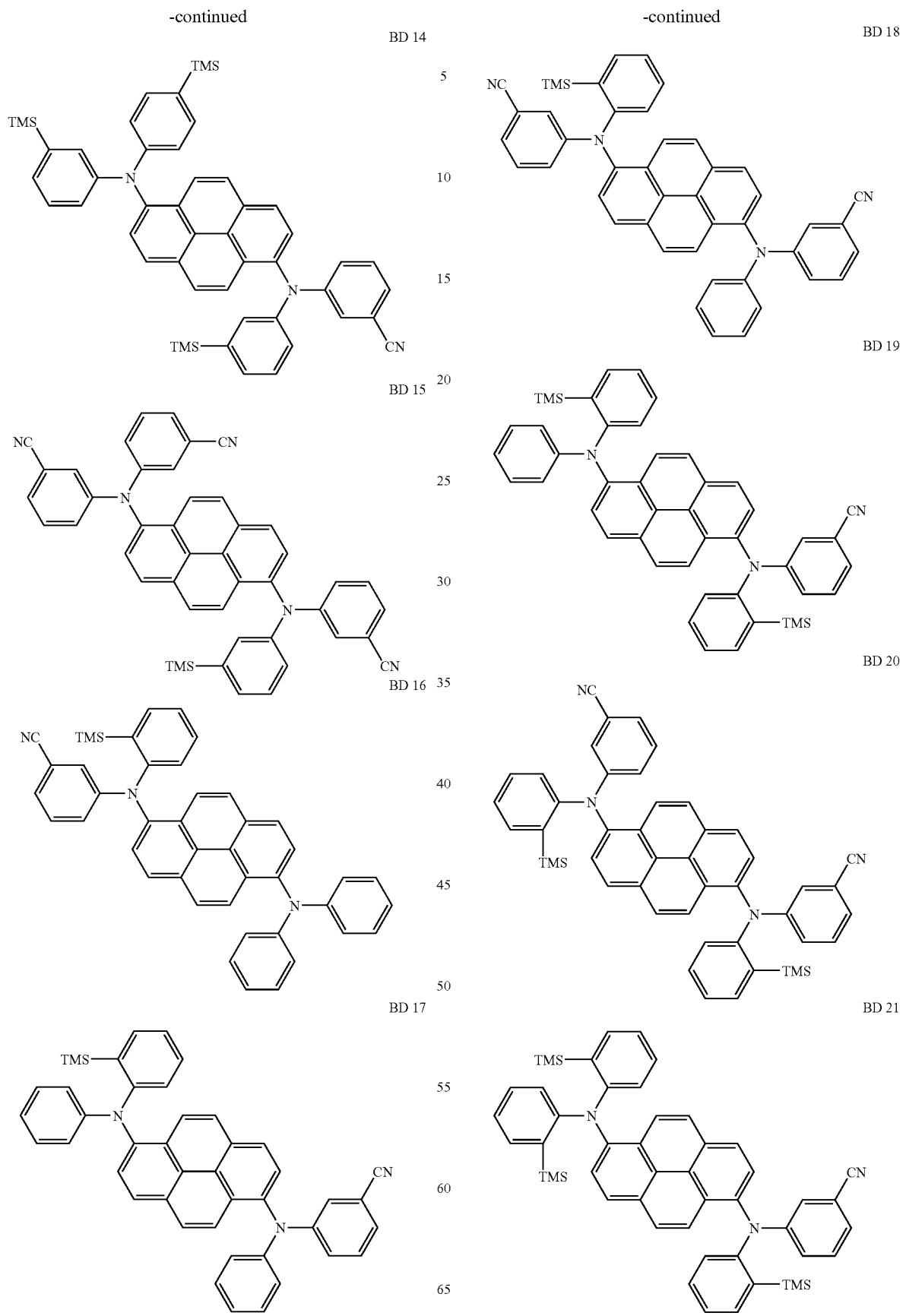

-continued
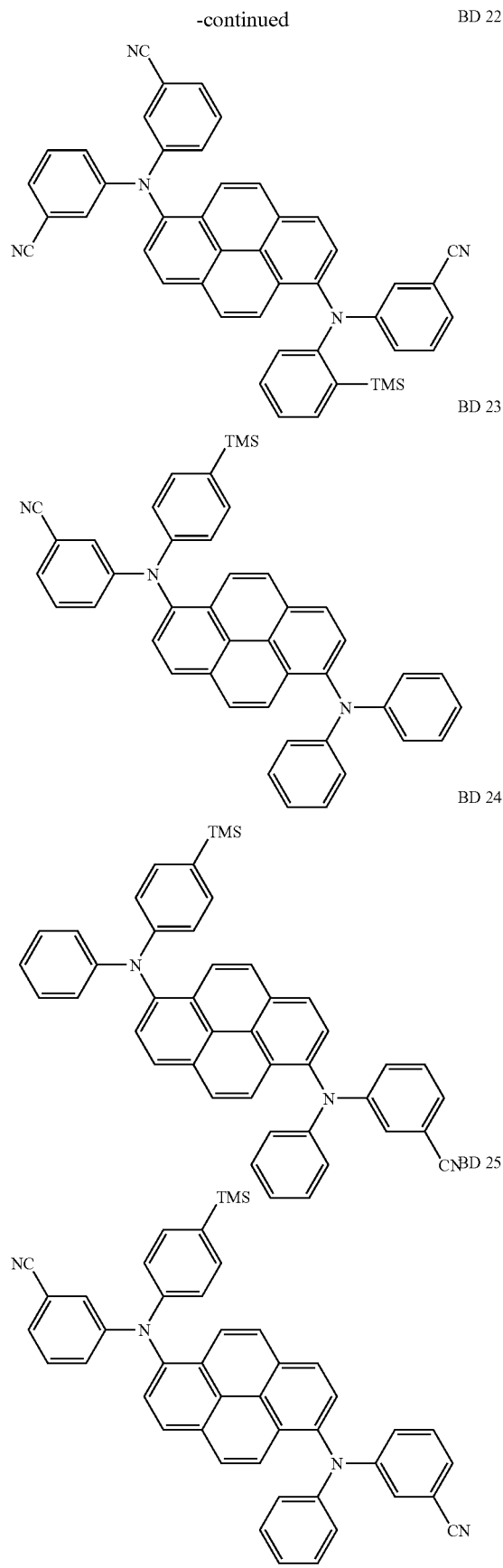
BD 22
BD 23
BD 24
BD 25
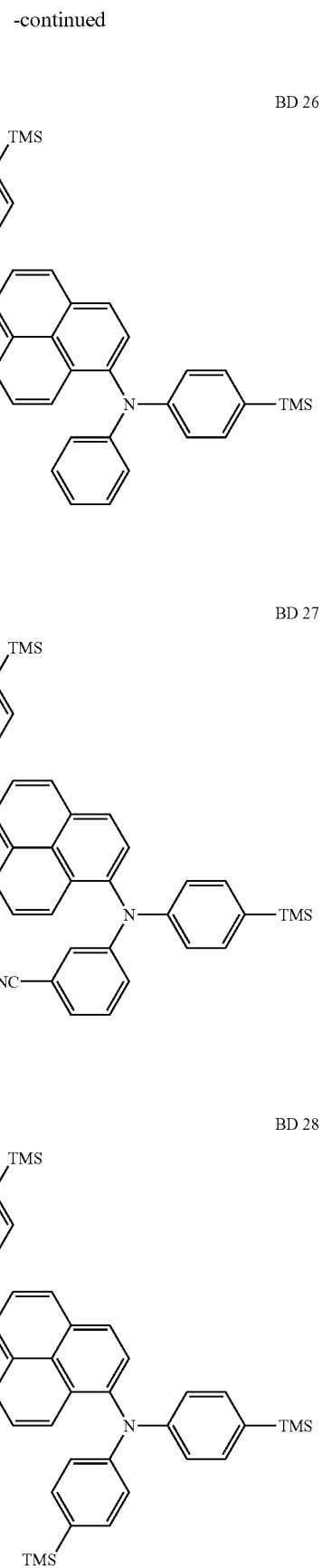
-continued
BD 26
BD 27
BD 28

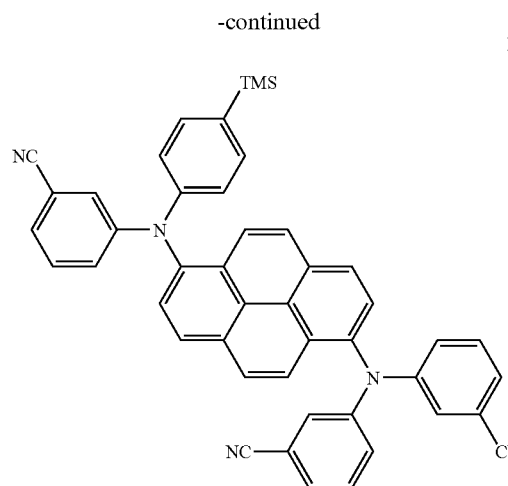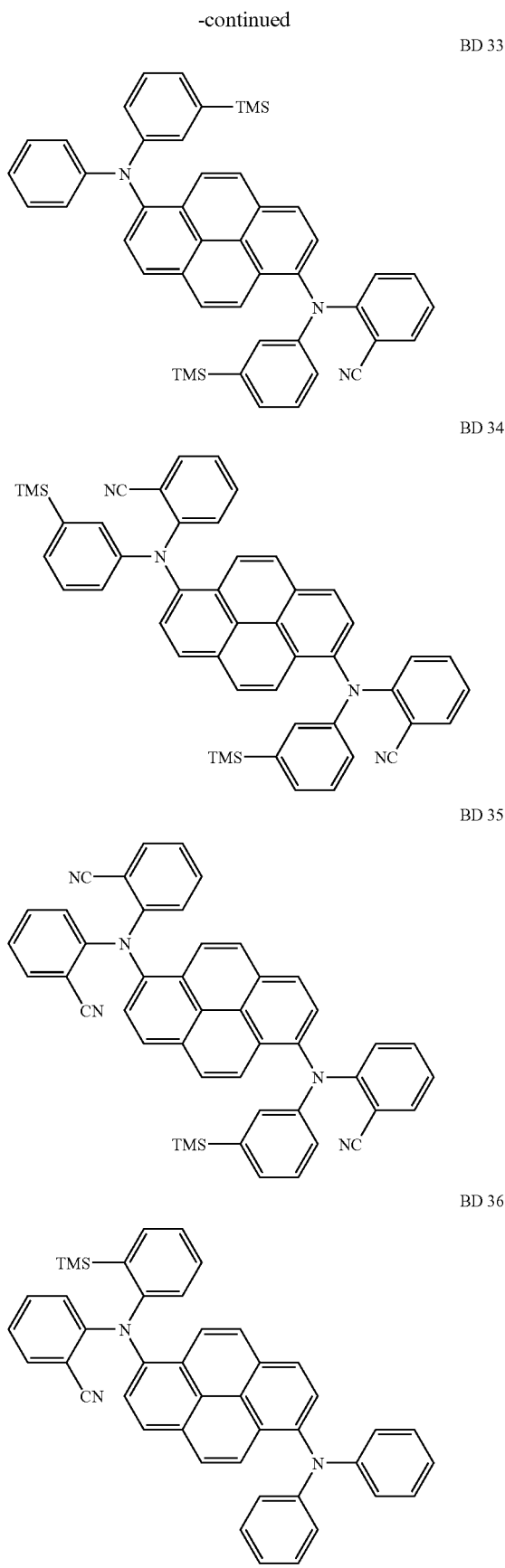

-continued
BD 37
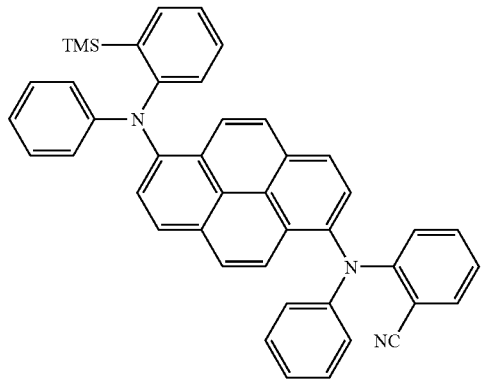
BD 38
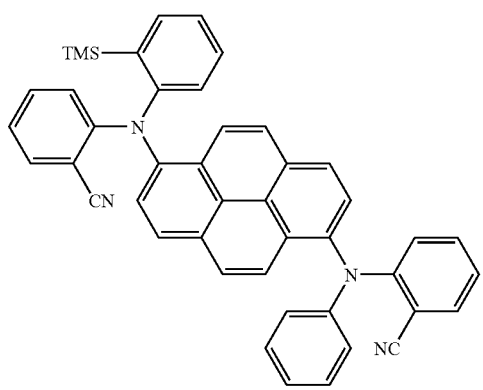
BD 39
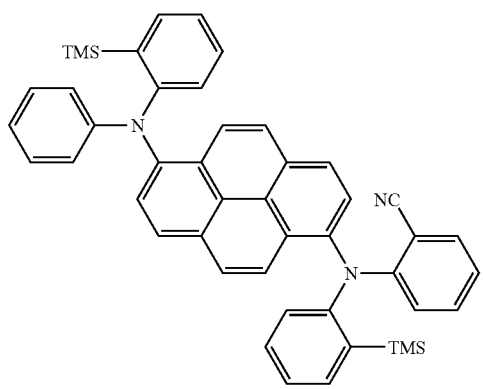
BD 40
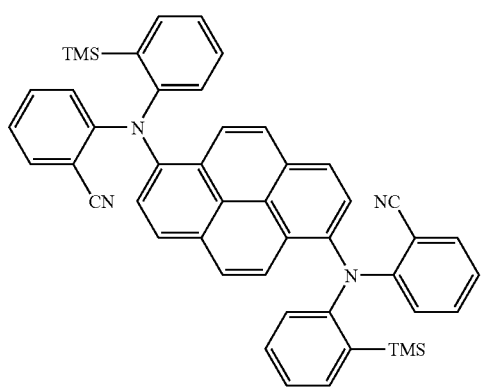
-continued
BD 41
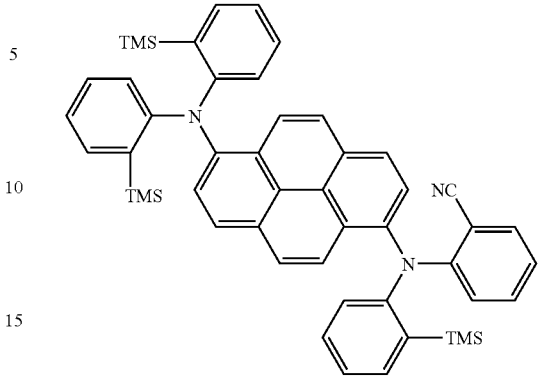
BD 42
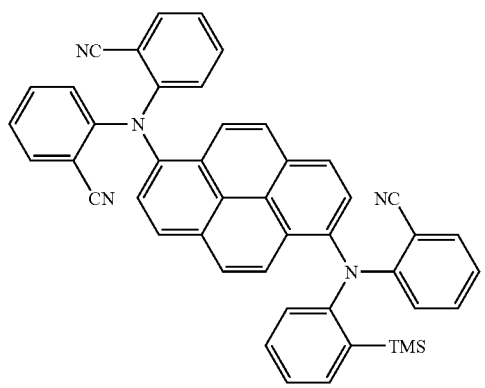
BD 43
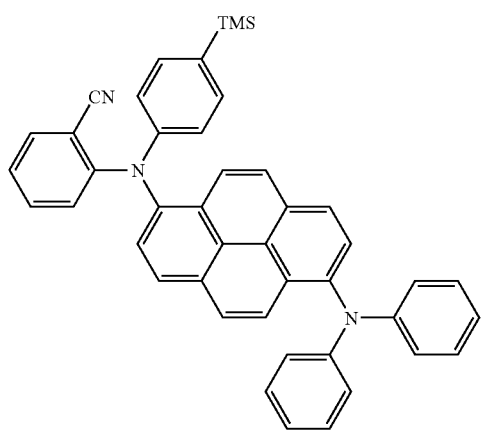
BD 44
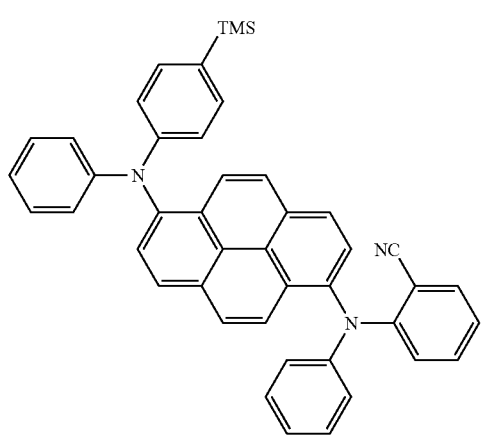

-continued
BD 45
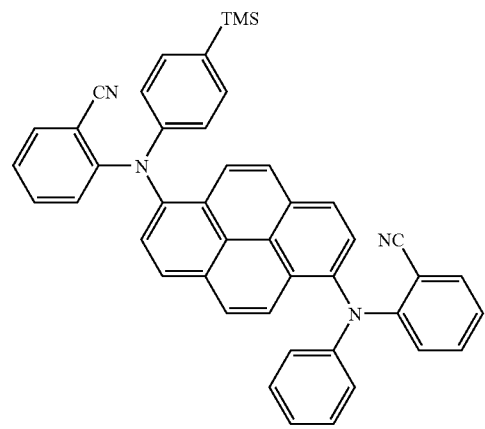
BD 46
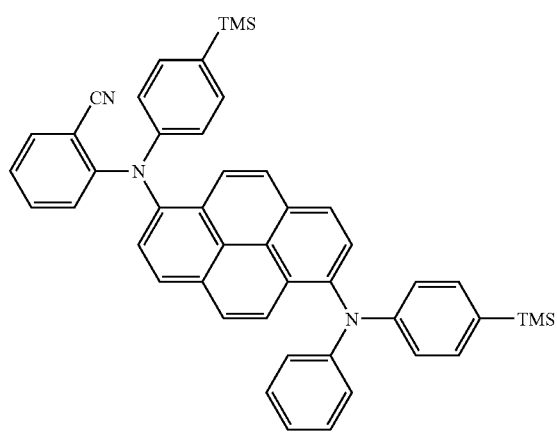
BD 47
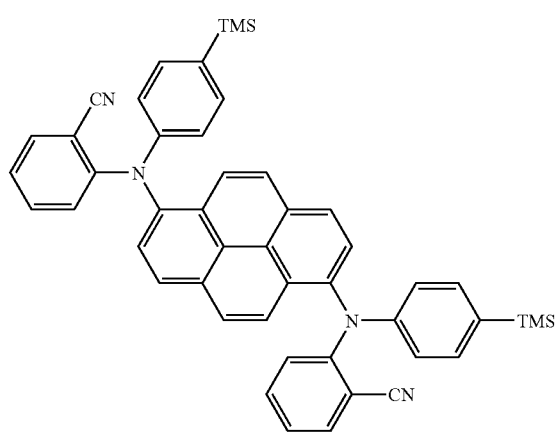
-continued
BD 48
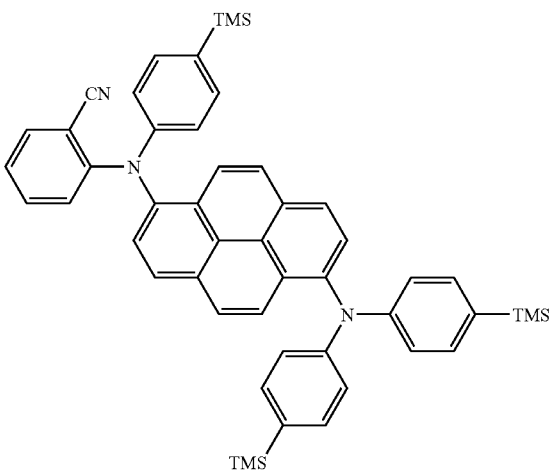
BD 49
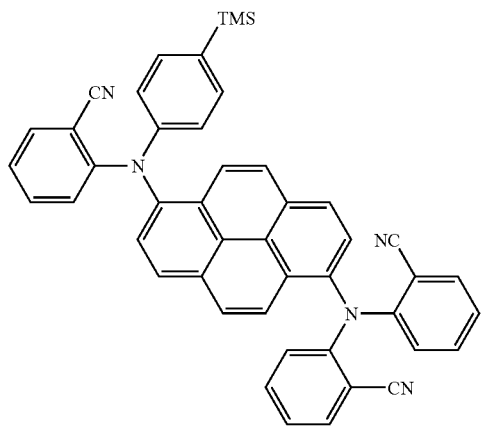
BD 50
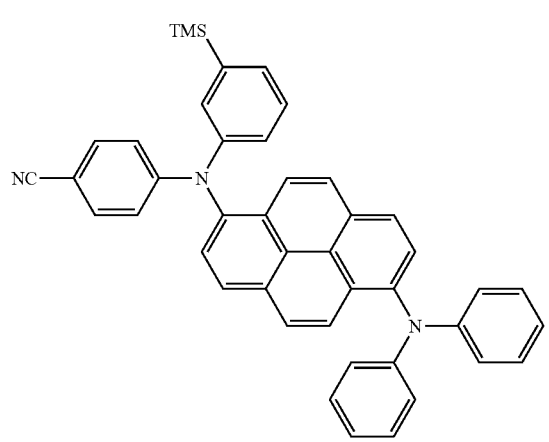

-continued
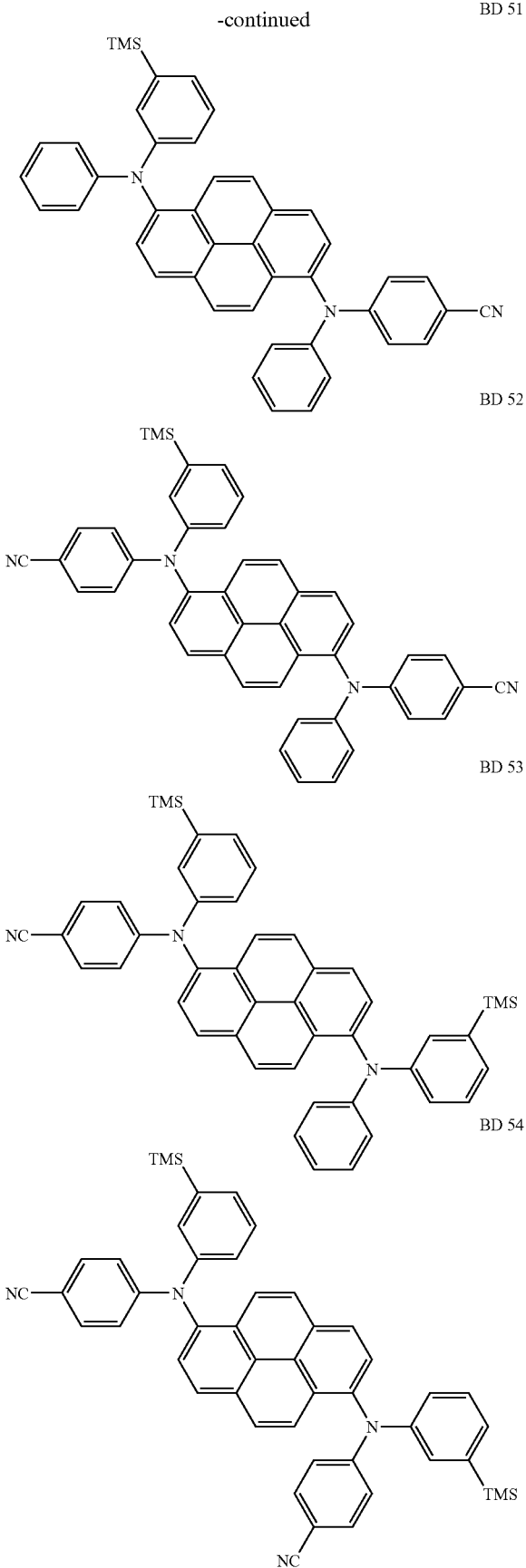
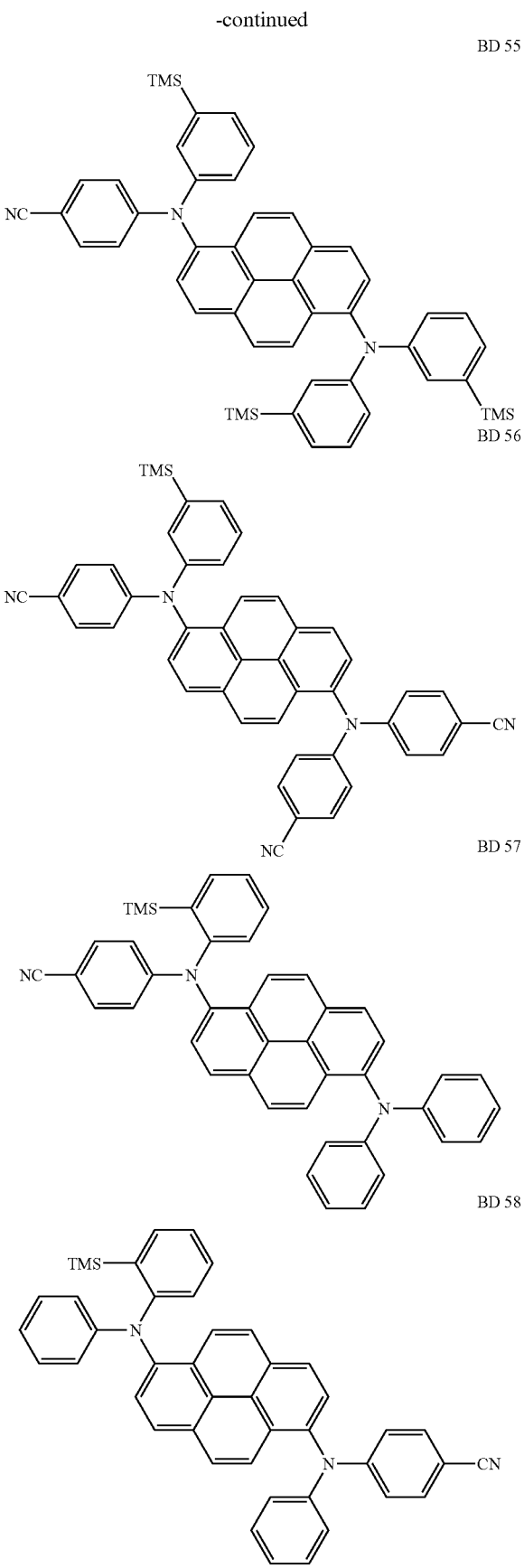

BD 59
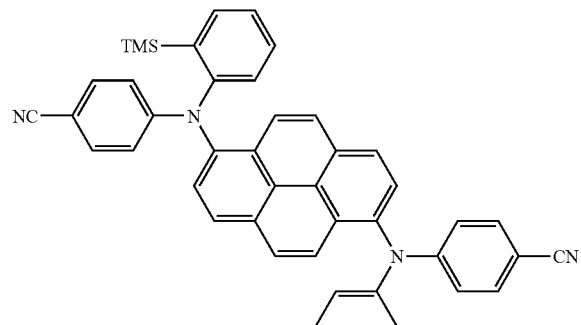
BD 60
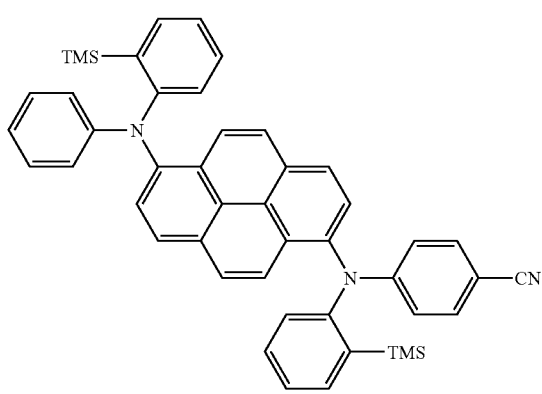
BD 61
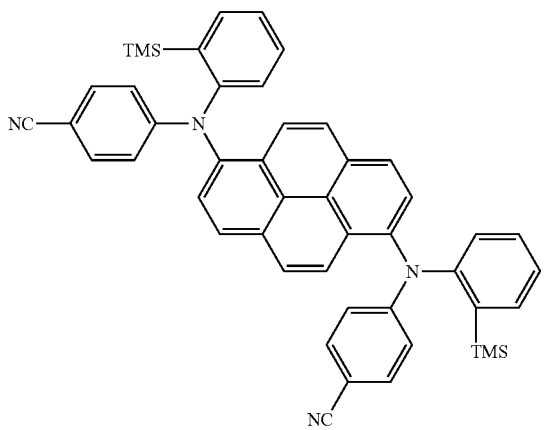
BD 62
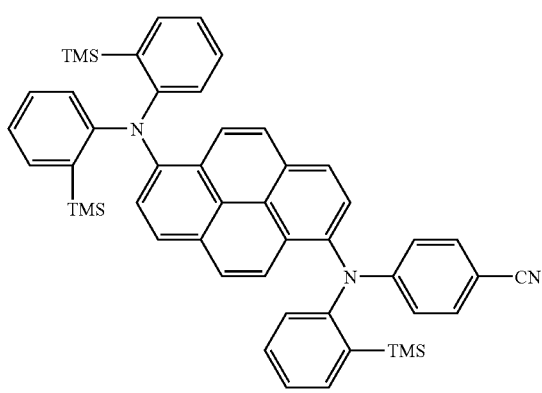
BD 63
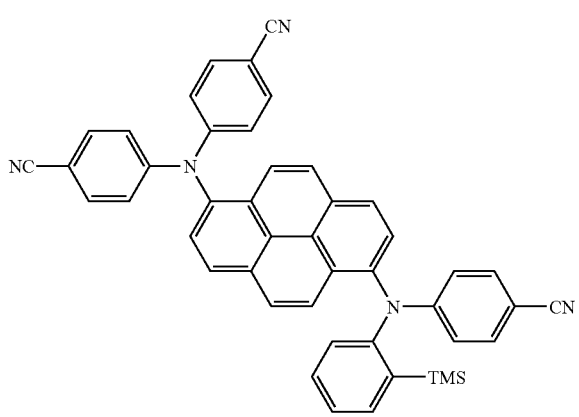
BD 64
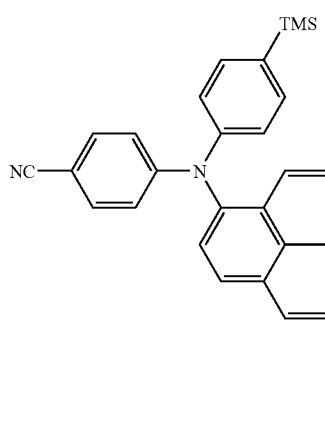
BD 65
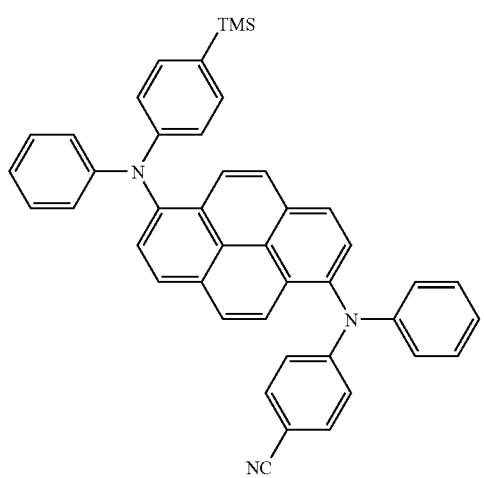

-continued
BD 66
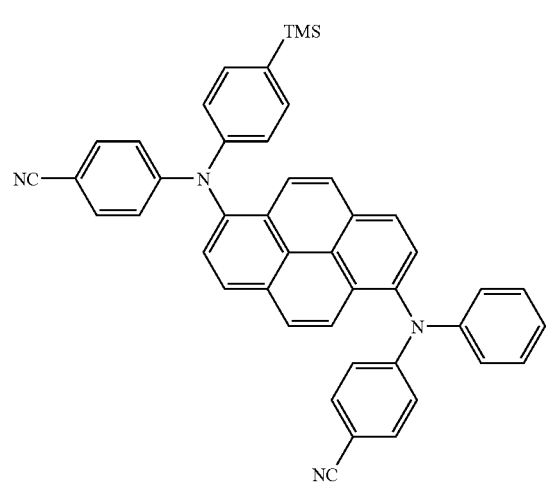
BD 67
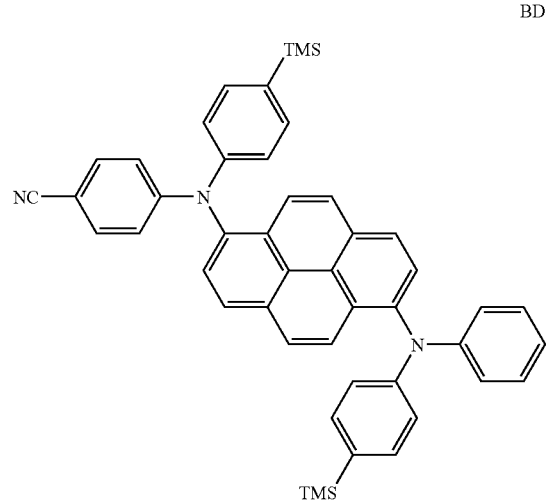
BD 68
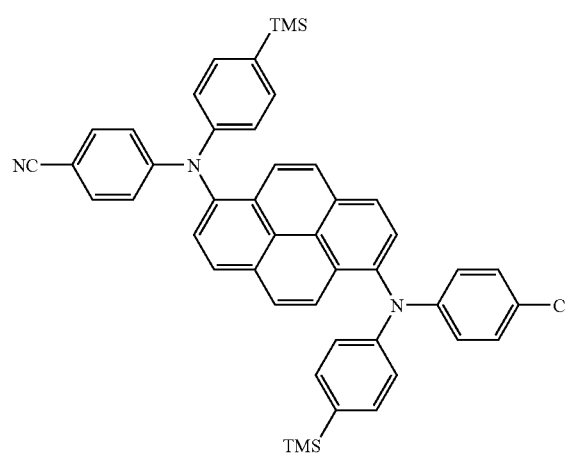
-continued
BD 69
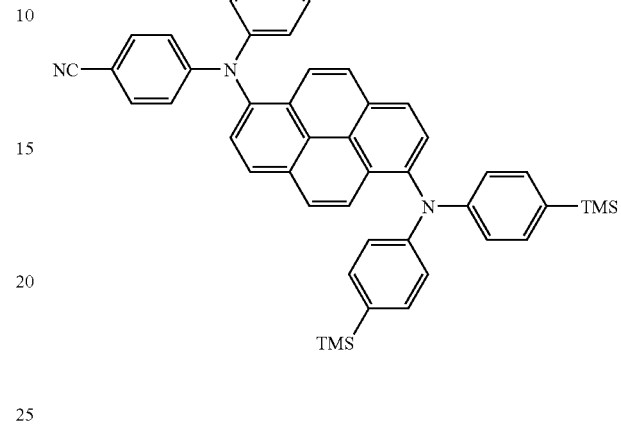
BD 70
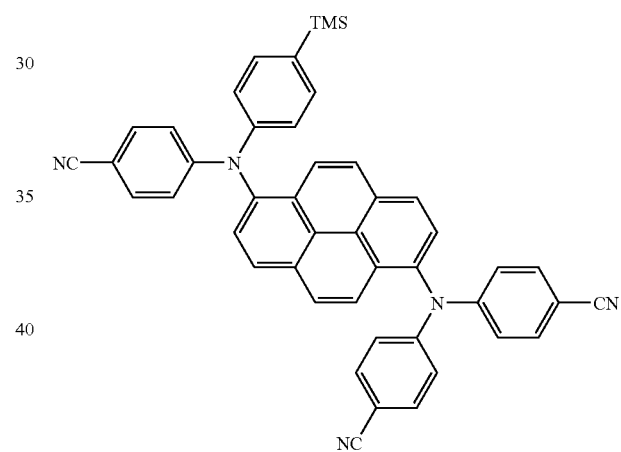
BD 71
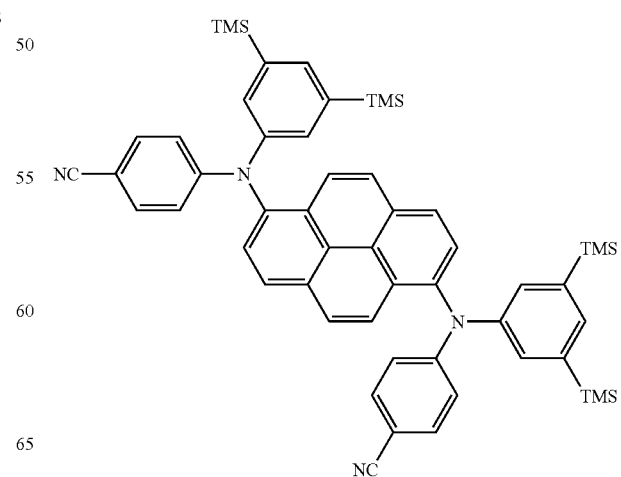

-continued
BD 72
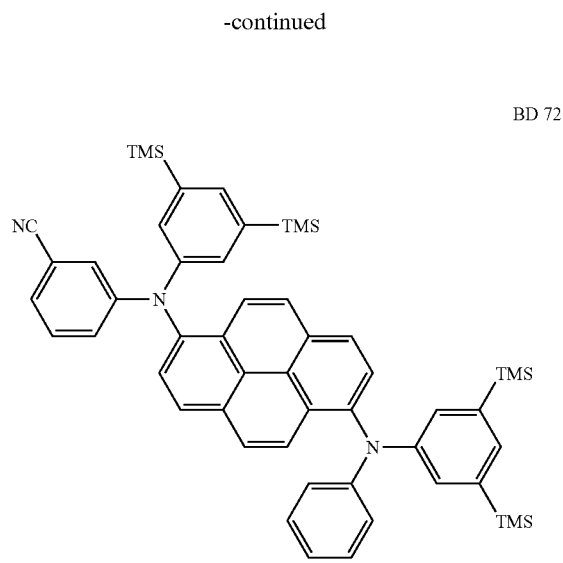
BD 73
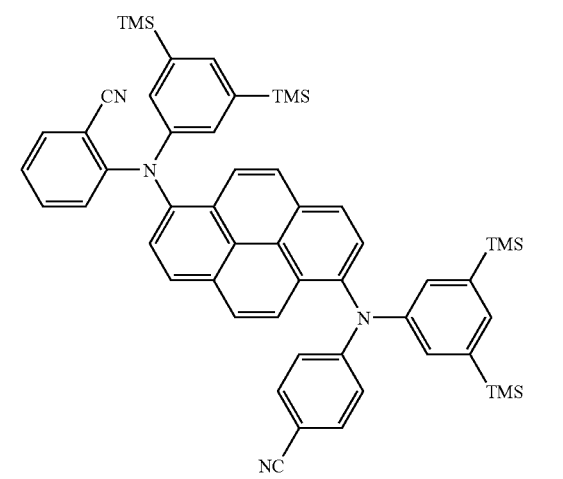
BD 74
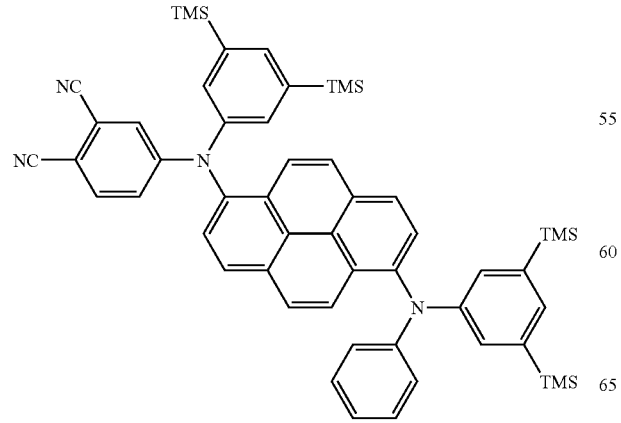
-continued
BD 75
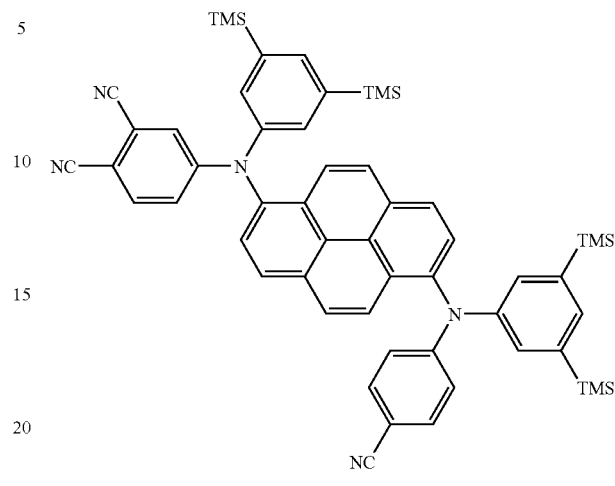
BD 76
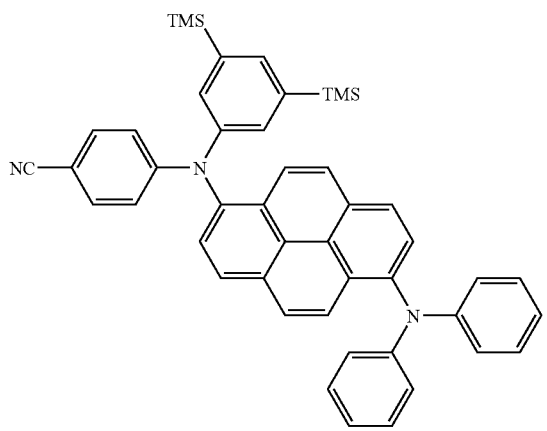
BD 77
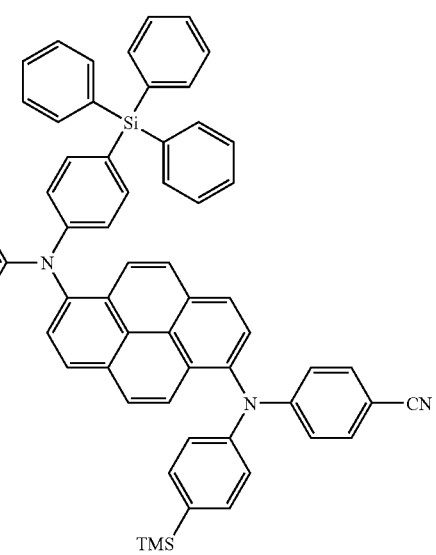

-continued

BD 78

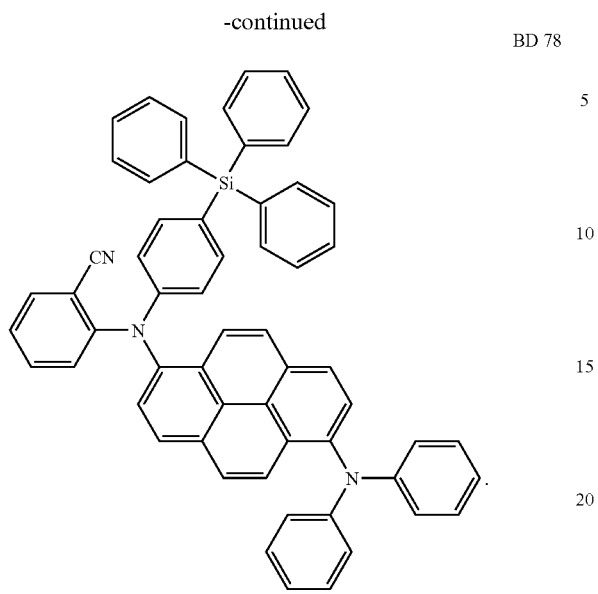

3. An organic electroluminescent device comprising an anode, an organic light-emitting layer and a cathode wherein the organic light-emitting layer includes the blue light-emitting compound according to claim 1.

4. The device according to claim 3, wherein the organic light-emitting layer further includes a compound selected from the following compounds (3):

(3)

BH-1

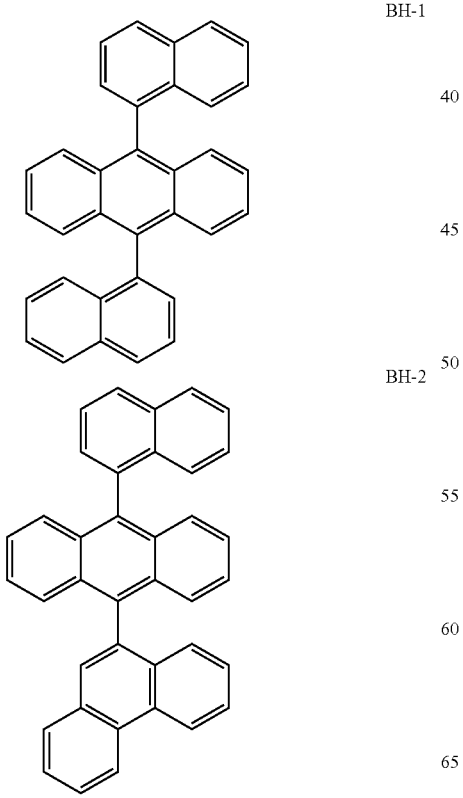

BH-2

-continued

BH-3

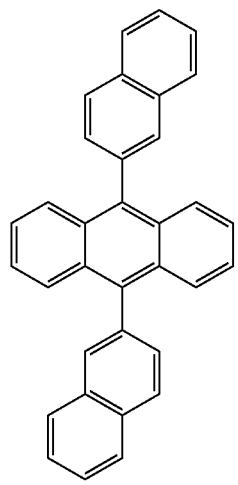

BH-4

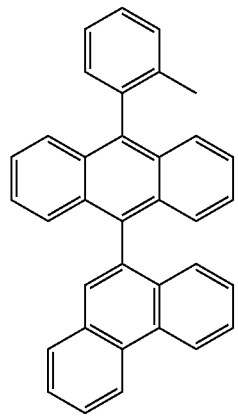

BH-5

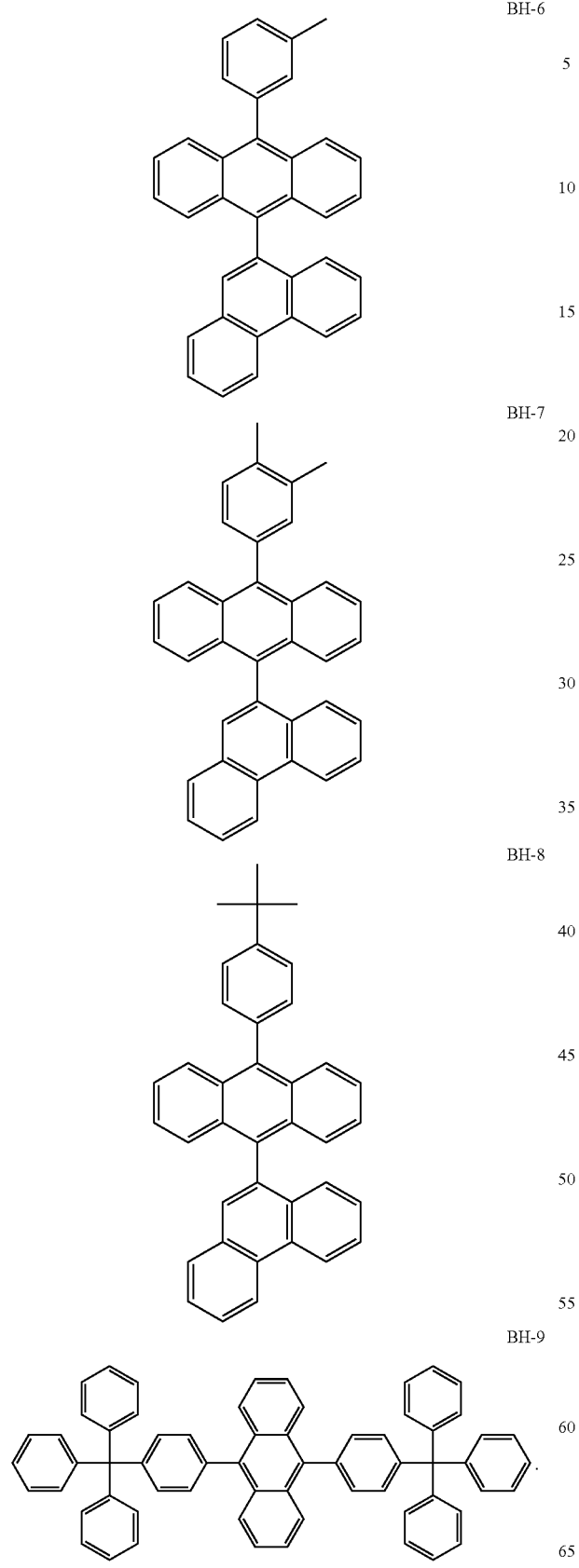
5. The device according to claim 3, further comprising a hole transport layer disposed between the anode and the organic light-emitting layer, and an electron transport layer disposed between the cathode and the organic light-emitting layer wherein the electron transport layer is formed of a compound selected from the following compounds (4):
(4)
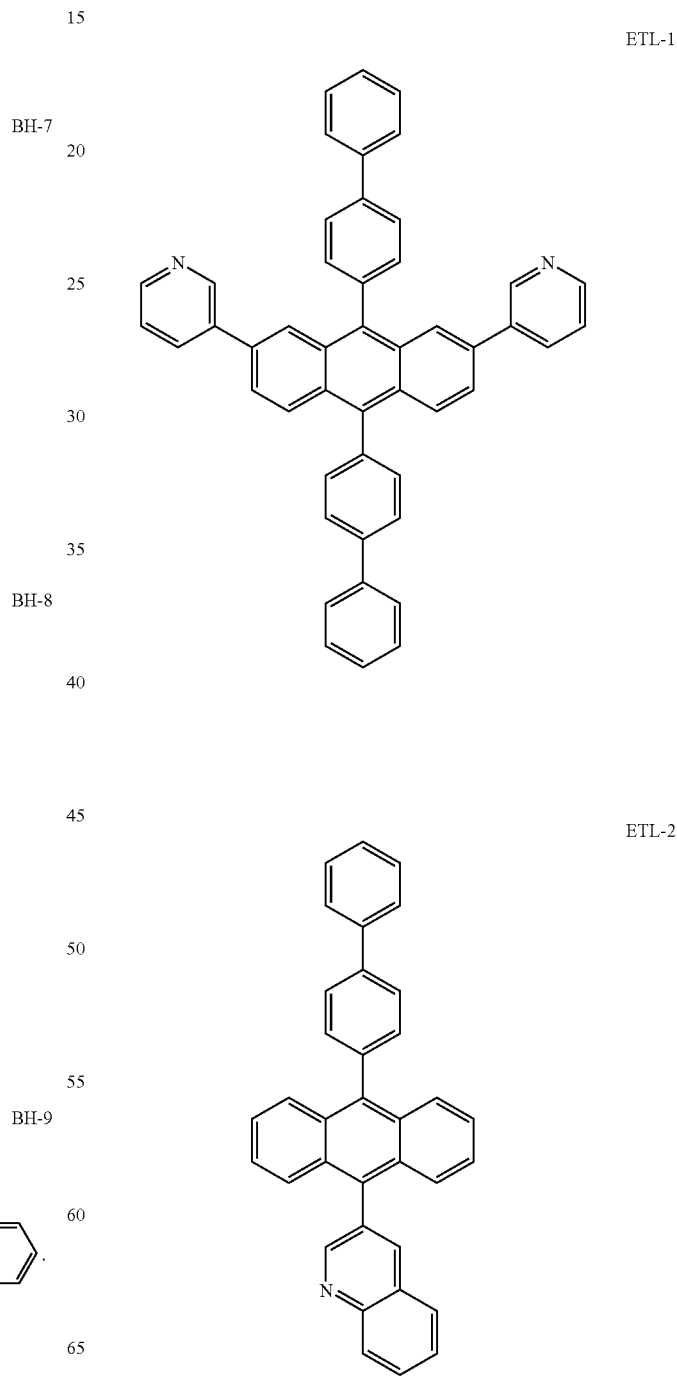

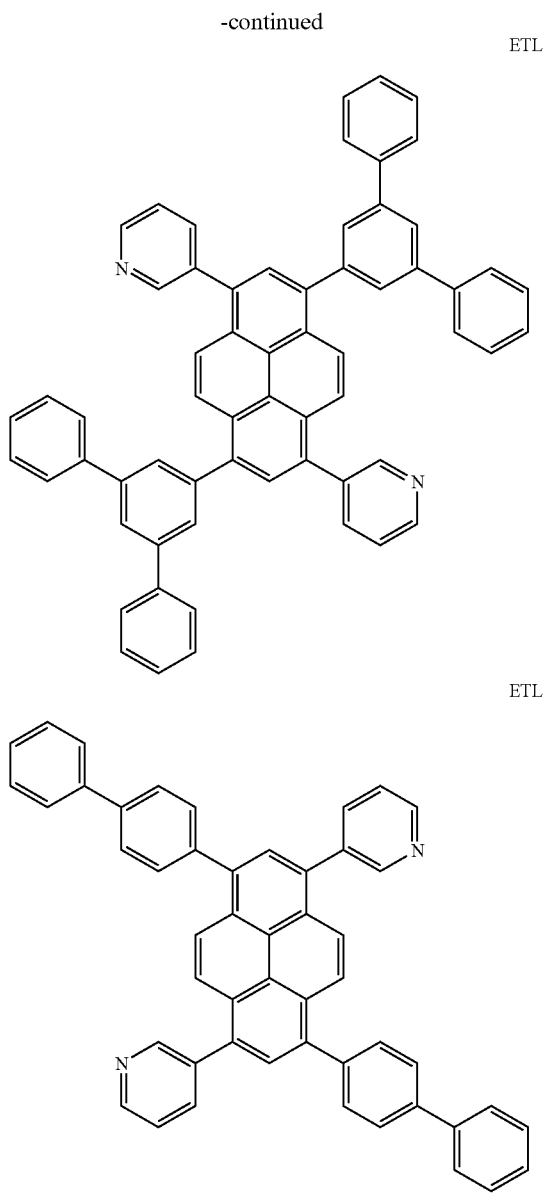

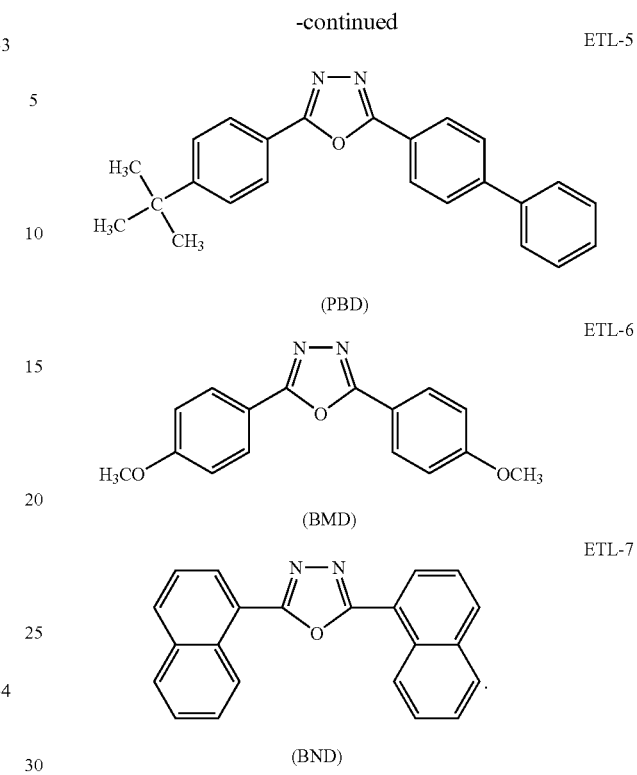

6. The device according to claim 5, further comprising a hole injecting layer disposed under the hole transport layer.

7. The device according to claim 5, further comprising an electron injecting layer disposed on the electron transport layer.

8. The device according to claim 5, wherein the hole transport layer is formed of N,N'-bis(3-methylphenyl)-N,N'-diphenyl-[1,1'-biphenyl]-4,4'-diamine (TPD) or N,N'-di(naphthalen-1-yl)-N,N'-diphenylbenzidine (α-NPD).

9. The device according to claim 6, wherein the hole injecting layer is formed of copper phthalocyanine (CuPc), 4,4',4"-tri(N-carbazolyl)triphenylamine (TCTA), 4,4',4"-tris(3-methylphenylphenylamino)triphenylamine (m-MTDATA) or DAPEB.

* * * * *